US008696690B2

(12) United States Patent
Almodovar

(10) Patent No.: US 8,696,690 B2
(45) Date of Patent: Apr. 15, 2014

(54) CONTINUOUS DRIVER WITH CHANGEABLE PARAMETERS

(76) Inventor: Luis Jose Almodovar, San Juan, PR (US)

( * ) Notice: Subject to any disclaimer, the term of this patent is extended or adjusted under 35 U.S.C. 154(b) by 556 days.

(21) Appl. No.: 12/552,258

(22) Filed: Sep. 1, 2009

(65) Prior Publication Data

US 2011/0054499 A1   Mar. 3, 2011

(51) Int. Cl.
*A61B 17/062* (2006.01)

(52) U.S. Cl.
USPC .......................................... 606/147; 606/144

(58) Field of Classification Search
USPC ......... 606/139, 144, 145, 147, 148, 222, 228, 606/232; 173/213
See application file for complete search history.

(56) References Cited

U.S. PATENT DOCUMENTS

| | | | | |
|---|---|---|---|---|
| 5,759,188 A * | 6/1998 | Yoon | ............................... | 606/147 |
| 5,860,992 A * | 1/1999 | Daniel et al. | ................... | 606/145 |
| 5,891,159 A * | 4/1999 | Sherman et al. | ............... | 606/144 |
| 5,954,731 A * | 9/1999 | Yoon | ............................... | 606/144 |
| 5,954,733 A * | 9/1999 | Yoon | ............................... | 606/147 |
| 5,957,937 A * | 9/1999 | Yoon | ............................... | 606/147 |
| 5,984,932 A * | 11/1999 | Yoon | ............................... | 606/147 |
| 5,993,466 A * | 11/1999 | Yoon | ............................... | 606/147 |
| 5,993,467 A * | 11/1999 | Yoon | ............................... | 606/147 |
| 6,071,289 A * | 6/2000 | Stefanchik et al. | ............ | 606/147 |
| 6,086,601 A * | 7/2000 | Yoon | ............................... | 606/148 |
| 6,126,665 A * | 10/2000 | Yoon | ............................... | 606/144 |
| 6,143,005 A * | 11/2000 | Yoon et al. | ..................... | 606/148 |
| 6,159,224 A * | 12/2000 | Yoon | ............................... | 606/147 |
| 6,224,614 B1 * | 5/2001 | Yoon | ............................... | 606/147 |
| 8,021,376 B2 * | 9/2011 | Takemoto et al. | ............ | 606/144 |
| 2003/0181924 A1* | 9/2003 | Yamamoto et al. | ........... | 606/144 |
| 2006/0020272 A1* | 1/2006 | Gildenberg | .................... | 606/144 |
| 2006/0282096 A1* | 12/2006 | Papa et al. | ..................... | 606/144 |
| 2007/0203507 A1* | 8/2007 | McLaughlin et al. | ......... | 606/144 |
| 2008/0071295 A1* | 3/2008 | Baxter et al. | ................... | 606/144 |
| 2009/0240263 A1* | 9/2009 | Kawai et al. | ................... | 606/147 |
| 2010/0042116 A1* | 2/2010 | Chui et al. | ...................... | 606/145 |
| 2010/0191259 A1* | 7/2010 | Suzuki et al. | .................. | 606/144 |
| 2011/0054499 A1* | 3/2011 | Almodovar | .................... | 606/147 |
| 2011/0152891 A1* | 6/2011 | McLawhorn et al. | .......... | 606/145 |

* cited by examiner

*Primary Examiner* — Thanh Truong
(74) *Attorney, Agent, or Firm* — Ferraiuoll LLC; Eugene J. Torres-Oyola

(57) ABSTRACT

The present invention relates generally to a continuous driver device with changeable parameters, more specifically, a continuous driver with changeable parameters used in surgical procedures such as suturing, wherein said continuous driver device is employed as a continuous suture rotational needle driver which enhances the tissue suturing procedure, particularly the one performed on restricted, deep and less accessible locations. The device incorporates a plurality of interactive portions comprising several extended members wherein said extended members are provided with rotational needle driving points at a distal end into a single device and is operated by the twist of a single knob. The use of the mechanism prevents problems associated with loss of needle control during the suturing procedure as well as the ones associated with the handedness of existing needle drivers.

20 Claims, 27 Drawing Sheets

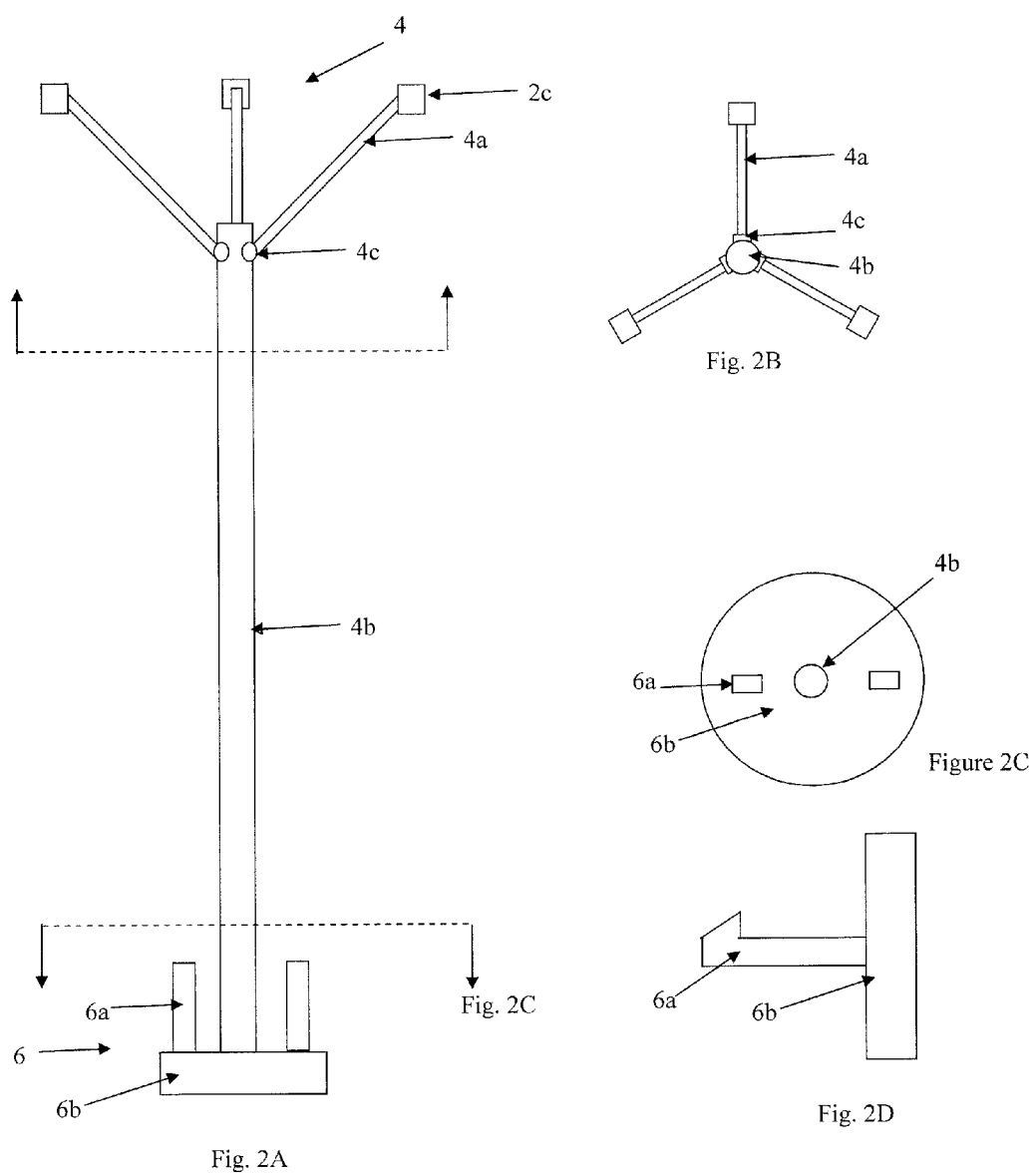

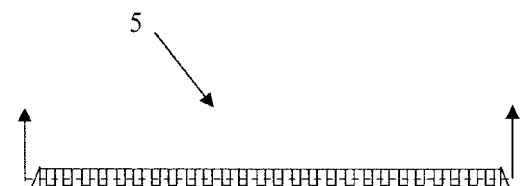
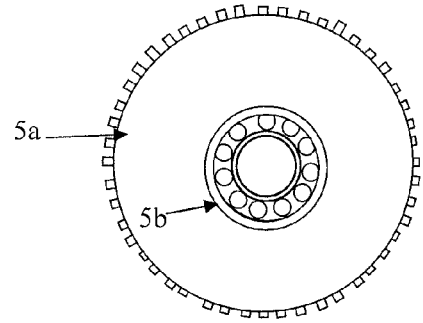
Fig. 3B
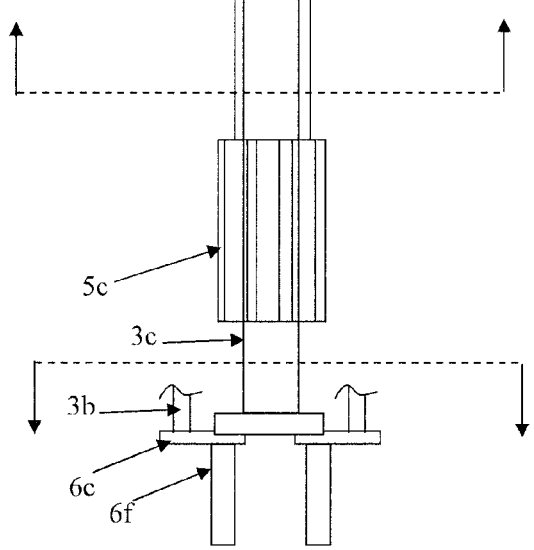
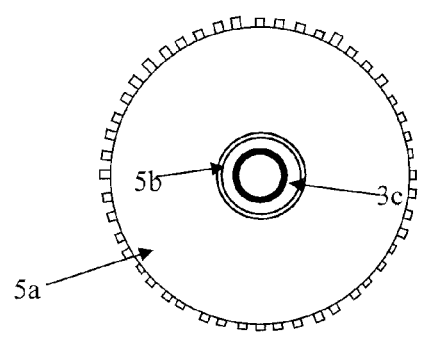
Fig. 3C
Fig. 3D
Fig. 3A
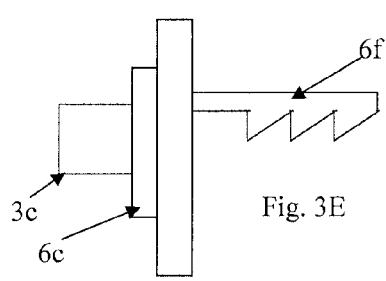
Fig. 3E

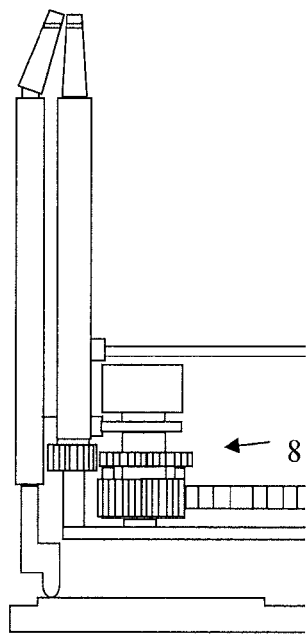
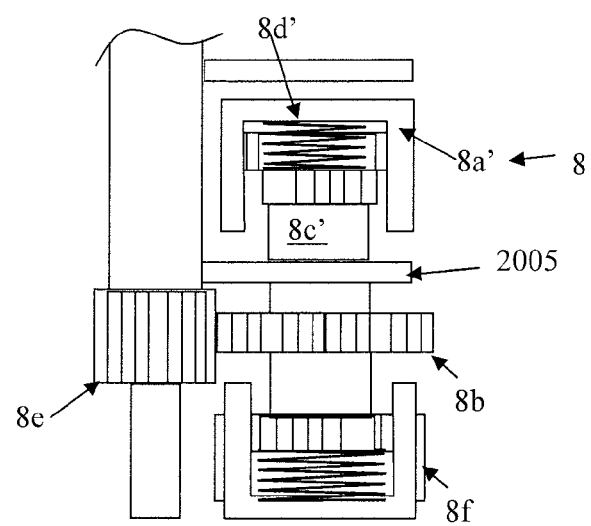
Fig. 17A  Fig. 17B
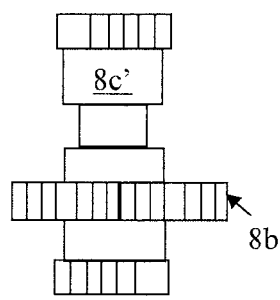
Fig. 17C

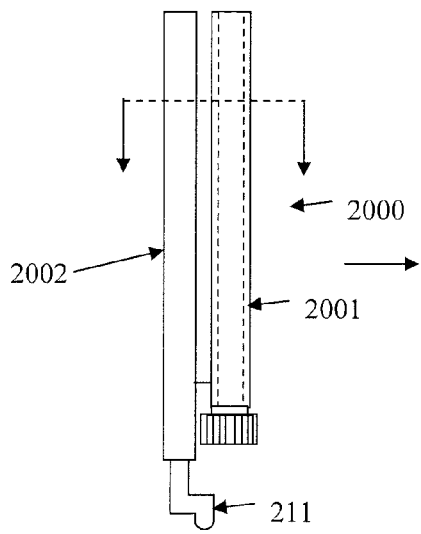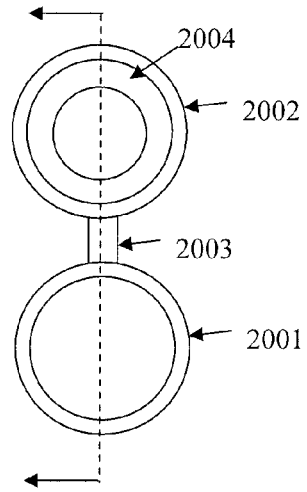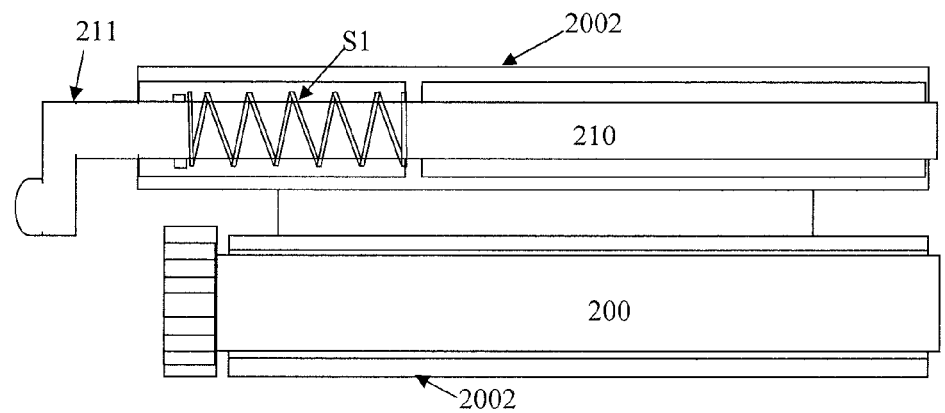
Fig.18A  Fig. 18B
Fig. 18C

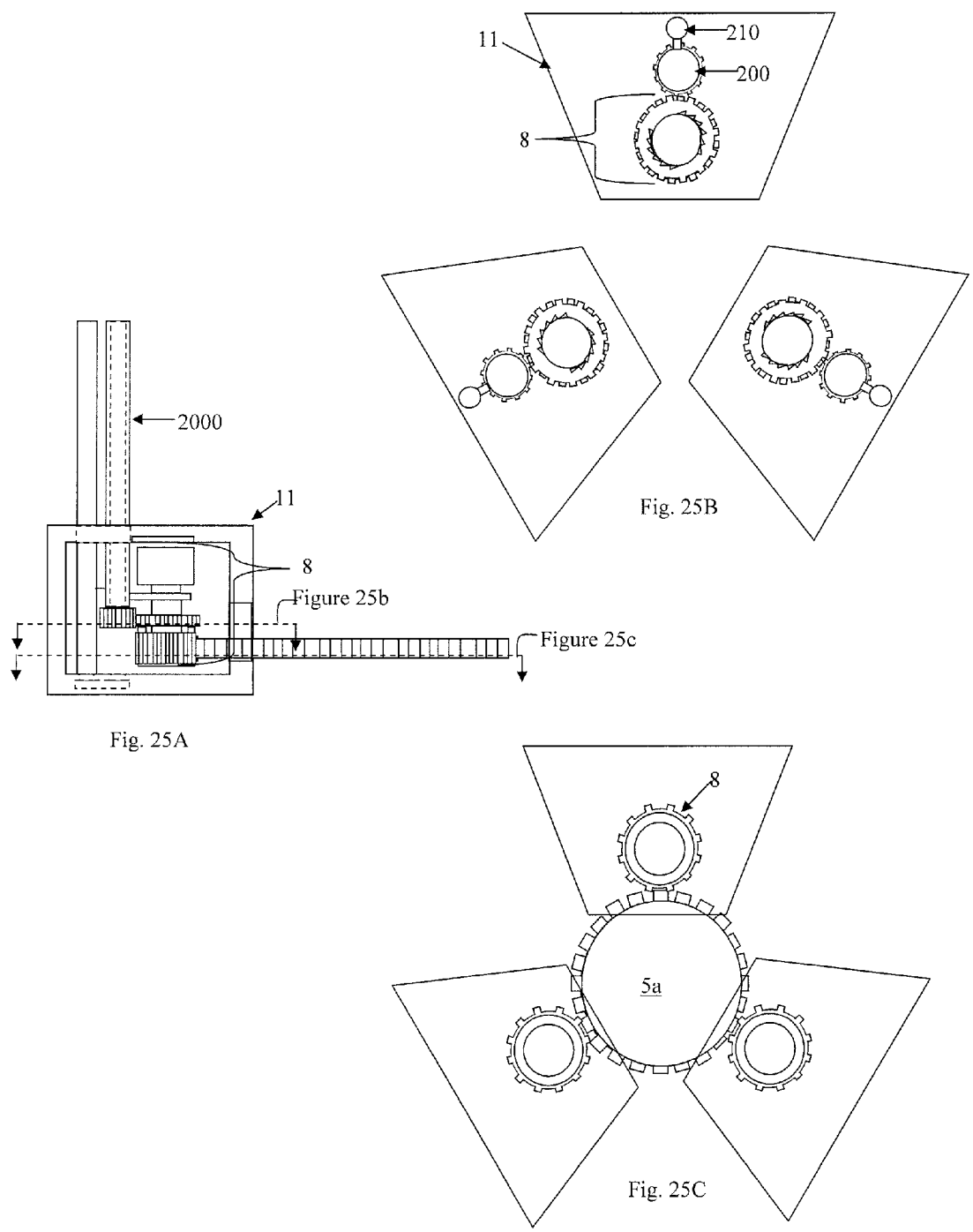

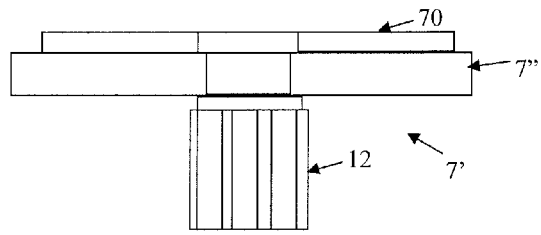
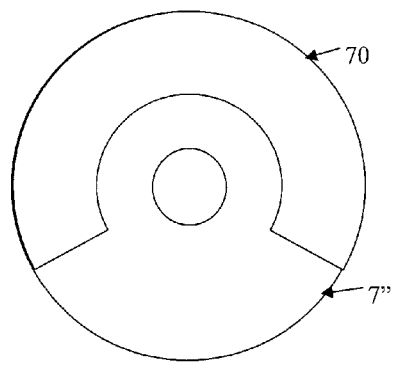
Fig. 28A
Fig. 28B
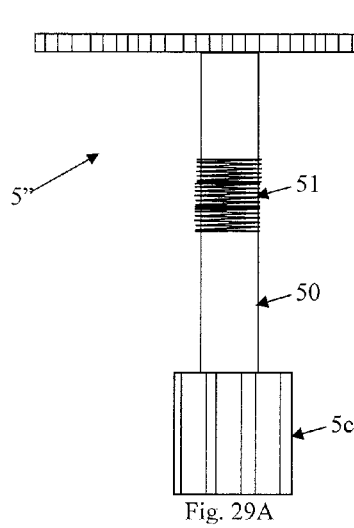
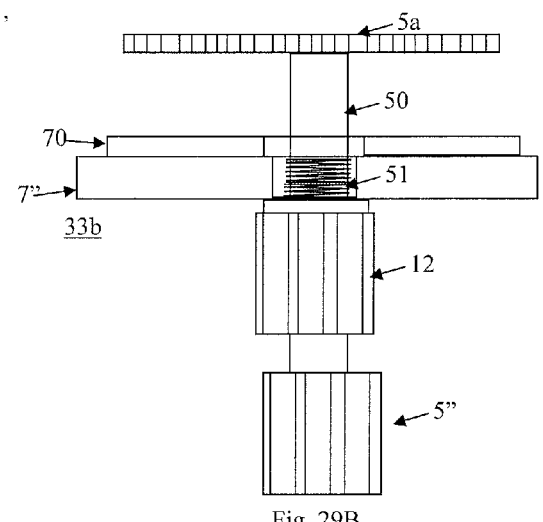
Fig. 29A
Fig. 29B
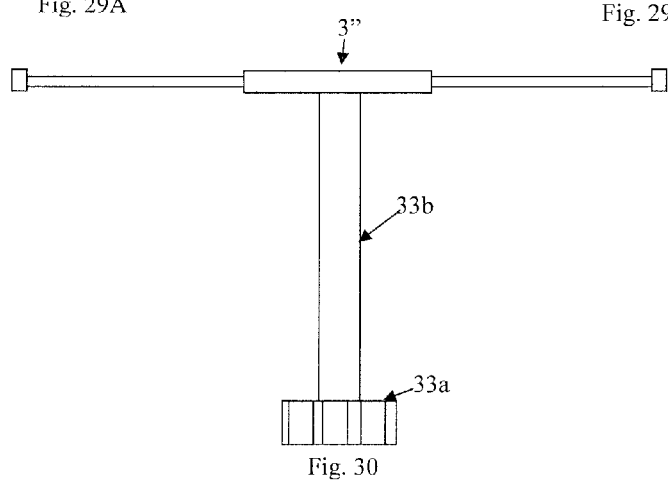
Fig. 30

CONTINUOUS DRIVER WITH CHANGEABLE PARAMETERS

STATEMENT REGARDING FEDERALLY SPONSORED RESEARCH AND DEVELOPMENT

N/A

RELATED APPLICATIONS

N/A

BACKGROUND OF INVENTION

1. Field of the Invention

The present invention relates generally to a continuous driver device with changeable parameters, more specifically, to a continuous driver with changeable parameters to be used in surgical procedure such as suturing, wherein said continuous driver device is employed in a continuous suture rotational needle driver which enhances the tissue suturing procedure. The device incorporates a plurality of interactive portions into a single device, each portion comprising several extended members wherein in said extended members are provided with rotational needle driving points at a distal end, and is wherein the device is operated by a actuator mechanism. The use of the mechanism prevents problems associated with loss of needle control during the suturing procedure as well as the ones associated with the handedness of existing needle drivers. It also enhances the control a surgeon has over the suturing needle by positioning a plurality of needle driving points at premeditated locations such that the needle will be driven by the device in a circular movement about the wound thus simplifying the steps to complete the suturing cycle. The needle driving system greatly simplifies the suturing procedure by combining the steps of the suturing procedure into a continuous cycle.

2. Background of the Invention

Surgical procedures have proliferated among the medical practice as new treatments are developed to effectively treat common and extraordinary conditions. The spectrum of invasiveness goes from simple tissue suturing of small open wounds to complicated procedures as those performed in vascular or neurological surgeries. It is undoubted that each and every step on any surgical procedure is of great importance and could cause negative consequences for the patient if it is inadequately performed. The suturing procedure, in particular, could end in serious consequences for the patient if negligently conducted, causing damages to adjacent tissues or even organs.

It is known that the suturing procedure consumes a considerable amount of time of the surgical treatment. Simplification of the suturing procedure by developing more effective suturing devices will reduce the time spent on that task and at the same time will reduce the risk of negative consequences arising from damages caused to adjacent tissues or organs.

With the increasing cost of healthcare, a new device and procedure are needed to simplify the suturing procedure and reduce the time required for the process, without sacrificing the quality and precision required for delicate sutures. There is also the need to reduce time and costs to create sutures when a large amount of patients need treatment. In times of war, natural disasters, or large-scale accidents, among others, there is a need to increase the speed of the suture procedure. In these cases, complications arise due to the amount of time the patient has to wait for treatment with an open wound. Open wounds are susceptible to infection and could result in serious blood loss. Decreasing the time a patient has to wait with an open wound could save lives in these cases.

Generally, the instruments used in suturing procedures are the suturing material, the suturing needle and the needle driver. Efforts have been made to reduce the suturing time and to enhance the suturing procedures' safety, but they have been focused on performing modifications to existing needle drivers.

One of the generally unattended deficiencies of the available needle drivers is the handedness of its designs. Ordinarily, needle drivers are designed to fit right handed users. The locking mechanisms and the direction of the curves at the end of the needle drivers are not designed for use by left-handed users. Thus, left handed users have difficulties performing the suturing procedure. Although some needle drivers are available in left-handed configurations, these have to be purchased separately. The additional purchases, the additional inventory, and the maintenance of the additional inventory further increases the cost involved with surgical and suturing procedures.

The difficulties encountered by left-handed doctors and hospital personnel increases the risks of negative outcomes for patients from wrong needle driver maneuverings. The latest improvements to suturing devices often fail at their intention of easing the handling of the device for this reason.

Therefore, it can be appreciated that there exists a prevalent necessity for new and improved suturing devices to perform safer and simplified suturing procedures. In this regard, the present invention substantially fulfills this need.

The suturing process executed with the needle drivers widely available today consists of a number of steps. These steps include, but are not limited to, grasping the needle with the needle driver, inserting the needle into the tissue, pushing the needle until it reaches the other side of the wound, letting go of the needle, and grasping the needle at the other side. The steps are repeated a number of times, depending on the size of the wound. Each step is susceptible to human error. Completing the cycle is a time-consuming process. There is a need for a procedure that will simplify the steps and shorten the time needed to complete the suturing cycle.

None of the prior art considered for this invention, taken either simply or in combination teaches the use of multiple needle driving points coupled to a geared mechanism as described above. In light of the foregoing, it will be appreciated that what is needed in the art is a suturing device capable of completing the suturing procedure in a simplified manner without the need of multiple devices.

SUMMARY OF THE INVENTION

The present invention overcomes the disadvantages of existing suture devices mentioned above by providing a device comprising interactive portions, a circumference adjuster, a locking mechanism, a rotational system, a linear motion system and a sequence control system.

Each interactive portion comprises several extended bodies, wherein each extended body comprises a distal end a proximal end and a main body, wherein said main body is located between said distal and proximal ends as one completed structure. Said interactive portion comprises action means to perform suturing, grasping, cutting, pushing and other motions wherein said action means comprises the distal end of a first extended body in combination with the distal end of a second extended body to perform an action over several materials including but not limited to, tissues, textiles and/or wires.

In the present invention the interactive portion is capable of shifting in more than one direction and/or performing several movements. For example, at least one extended body of the interactive portion rotates upon itself or/and move linearly to perform a task such as grasping or cutting and/or transfer for one position to another in order to modify distance between the interactive portions.

In order to achieve the movement of said interactive portions each interactive portion is coupled and mechanically connected to a system that provides at least one of the desired motions. In the instance case the circumference adjuster, rotational system and linear motion systems are mechanically connected to interactive portion.

The circumference adjuster comprises circumference changing means to change the distance between the interactive portions by angular displacement and/or linear motion of the interactive portions, wherein said circumference changing means comprises gears, bearings and circumference change actuators. Further, the device comprises a locking mechanism in order to lock or hold the interactive portions at a preferred circumference.

The rotational system comprises rotational motion means to rotate at least one extended body of the interactive portion upon itself, wherein said rotational motion means comprises a rotational motion actuator mechanically connected to several gears with different ratios in order to achieve a desired rotation at said interactive portion.

The linear motion system comprises linear motion means to provide a desired linear motion at least one of the distal ends of each interactive portion to, open close or compress said interactive portion. Said linear motion means comprises a linear motion actuator connected to several elements, including but not limited to, gears with a particular ratio and resilient material. The linear motion system is preferred to execute the linear motion for a specific time at each interactive portion. Therefore the linear motion system is designed to comprise a linear movement sequence control, wherein linear movement sequence control uses part of the linear motion means elements.

The present invention achieves the combination of several systems in a single apparatus wherein several interactive portions are provided with changeable circumference properties wherein at the same time the apparatus provides distal ends with linear sequence control movement and/or a rotational movement in order to facilitate and efficiently speed up several procedures such as suturing, grasping, cutting, wiring and other procedures that interact with a material such as but not limit to tissues, textile, wires and others.

As an example, the present embodiments make use of the present invention to provide an effective suturing device that enhances the maneuvering and safety of suturing procedures, as well as decreasing the time required to complete a suturing procedure.

The disclosed embodiments consist of a suturing device that comprises a plurality of interactive portion comprising extended members wherein each extended member includes a distal end include action means, such as needle driving points at a distal end of the of the extended members, wherein each extended member is adequately placed such that the needle's movement through the driving points completes one cycle of the suturing procedure. Each interactive portion comprises two rods as extended member that will rotate in opposite directions. The needle will be held between the rods and will be driven by the rotation of the rods. Prior to the release from the starting needle driving point, the needle will be inserted between the next needle driving point in the cycle. As the motion continues, the needle is released from the starting point and movement is driven by the next point. Further before release from the next point, the needle will be grasped by the following point, and so forth as part of the sequence control.

The needle driving points are located around a circumference that can be adapted to fit the curvature of a particular needle. With this feature, a single device can be used for a wide range of wound types and sizes, from small wounds resulting from endoscopic procedures to large wounds resulting from accidents or invasive surgery.

The device is driven by several elements such as geared mechanism that will rotate the rods and move the needle across the cycle. The mechanism includes but is not limited to a linear motion system comprising a cam system that will increase or decrease the pressure between the rods at different points within the cycle, such that the rods tighten or release the needle as required as part of the sequence control.

The use of several elements, such as a geared mechanism, provides the desired motion at the interactive portions and at the same time the present arrangement simplifies the use of the device. The device comprises several actuators to transfer a rotational, turning or spinning motion into a desired change in the apparatus parameter. For example a knob turned by the user is coupled to a main gear which controls the rotation of the driven rods. The slave rods are controlled by the rotation of the driven rods. The rotation of the needle is controlled by the rotation of the driven and slave rods. The cam system is also controlled by the rotation of the knob. In conclusion, the functionality of the entire system is controlled by the rotation of a single knob. The suturing procedure is in turn greatly simplified. By achieving a simplified design that will complete the steps of a suturing cycle with the twist of single knob, the invention provides a number of possibilities for further development. The advances in medical technology are moving towards machine-powered automatic devices which increase the precision and decrease the risk of human error. The simplicity of the proposed invention can easily be coupled with machines of this kind.

Additional applications associated with the proposed invention, such as sewing, crafts and electronics, also benefit from the simplicity of the device and its capability to be coupled with automatic machines.

The device has been designed for convenient use of right and left-handed users. The need for a reduced number of suturing devices and the increased speed of the suturing procedure will no doubt have a positive impact in the cost of surgical and emergency room procedures.

Therefore one of objects of the present invention is to provide a continuous driver with changeable parameters to be used in surgical procedure such as suturing, wherein said continuous driver device is employed in a continuous suture rotational needle driver which enhances the tissue suturing procedures.

Another object of the present invention is to provide a surgical suturing device that eases the suturing procedure.

Another object of the present invention is to provide a surgical suturing device that reduces cost of surgical and emergency room procedures.

Another object of the invention is to provide a device that will complete an entire suturing cycle with one simple motion without the need to reposition the needle.

Another object of the present invention is to provide a device designed for convenient use of right and left-handed users.

Yet another object of the present invention is to provide a device wherein the change in parameters is controlled by at least one actuator located at a comfortable position for the hand and/or thumb for a simple driven action.

Furthermore, the present invention overcomes the inability of the prior art to foresee the need of an ergonomic suturing needle driver that permits left and right handed users to performed safe suturing procedures. The present apparatus is intended to provide an ergonomic suturing device comprising: (i) a plurality of needle driving points located in premeditated positions such that movement of the needle through the points completes one cycle of the suturing procedure; and (ii) a geared mechanism that allows the suturing procedure to be executed with the rotation of a single knob.

The system of the invention itself, both as to its configuration and its mode of operation will be best understood, and additional objects and advantages thereof will become apparent, by the following detailed description of a preferred embodiment taken in conjunction with the accompanying drawing.

When the word "invention" is used in this specification, the word "invention" includes "inventions", that is, the plural of "invention". By stating "invention", the Applicant does not in any way admit that the present application does not include more the one patentable and non-obviously distinct invention and Applicant maintains that the present application may include more than one patentable and non-obviously distinct invention. The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

FIG. 2A-2D shows the first embodiment circumference adjuster components.

FIG. 3A-3E shows first embodiment rotational system components

FIG. 17A-17C shows part of the second embodiment two way circumference adjuster components FIG. 18A-18C shows the second embodiment extended member housing

FIG. 25A-25C shows the third embodiment interchangeable box with several elements from different sub systems coupled to the rotational system main gear.

FIG. 28A-28B shows part of the third embodiment linear motion system with a contact distal end adjustment mechanism.

FIG. 29A-29B shows part of the third embodiment rotational system in combination with the linear motion system.

FIG. 30 shows part of the third embodiment circumference adjuster components.

DESCRIPTION OF THE PREFERRED EMBODIMENT

Figure 1:
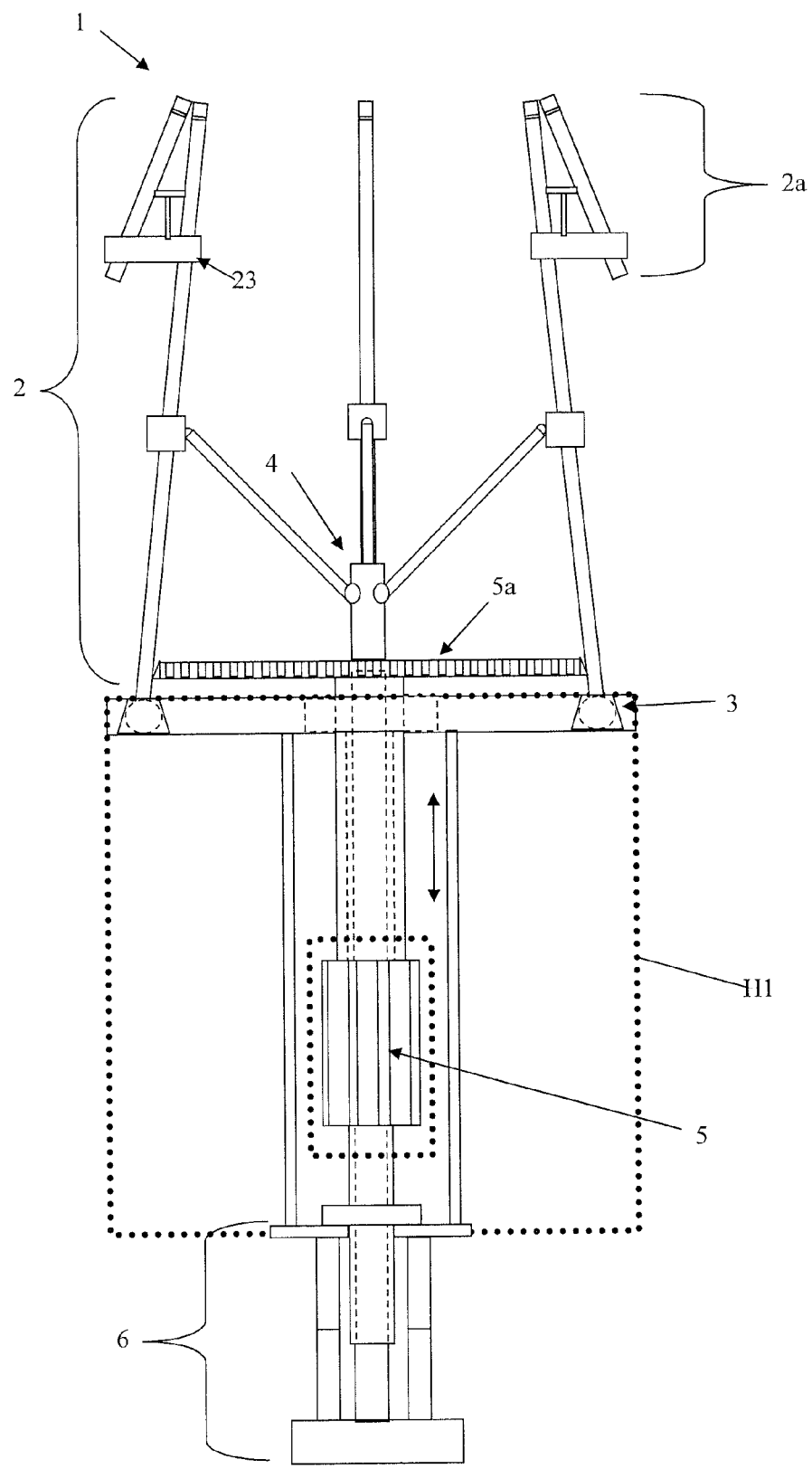
FIG. 1 shows a first embodiment employing a continuous driver device with changeable parameters.

FIG. 1 shows a first embodiment employing a continuous driver device 1 with changeable parameters as suturing device wherein said continuous driver device comprises a interactive portions 2, a circumference adjuster system 4, locking mechanism 6, a rotational system 5, at least a linear motion system 7, a sequence control system comprising several linear motion systems 7 mechanically connected, and a housing H1 comprising a frame 3. All element or part are made by different material wherein said material are selected depending on the field the device is going to be employed.

For example, employing the continuous driver 1 as a suturing device requires at least a needle grasping action combined rotational motion in order to produce a continuous circumferential motion of the needle during the suturing procedure. The translation of the needle 111 during continuous circumferential motion is limited to a particular radius, wherein said particular or preferred radius depend most of the time of the wound to be sutured. The first embodiment, as mentioned before, comprises a circumference adjuster 4, as shown in FIG. 2A-2D, wherein said circumference adjuster fulfill the purpose providing a desired radius subject to a radius displacement of the needle 111.

The circumference adjuster system for the first embodiment, as shown in FIG. 2A-FIG. 2D, comprises a shaft, such as central rod 4b, wherein said central rod 4b comprises two distal ends, wherein the first distal end comprises an expandable member or pivoting legs 4a and at the second distal end comprises locking means 6. Each pivoting leg, as shown in FIG. 1, contacts said interactive portion 2 maintaining a constant distance between said interactive portions 2. The connection between the interactive portion 2 and the pivoting leg 4a is accomplished by a rotational holder 2c. Each rotational holder 2c comprises a bearing means, such that the part of the interactive portion 2 can rotate within it. The second distal end of the central rod 4b, comprises locking means 6 as mentioned before wherein said locking means 6 comprises a platform 6b. The locking means 6 also serves as the circumference adjuster actuator wherein said device circumference is increased by pushing said platform 6b forward. In other words pushing the central rod 4b forward causes the pivoting legs to push the interactive portions 2 outward. In order to control the displacement and/or to fix the circumference at a desired radius the platform 6b comprises extended pieces having hook shapes 6a that interact with another portion of the locking system located at the static structure or frame 3.

Further the central rod 4b is assembled to be slipped along the center axis of the device, within the hollow central shaft 5b of the rotational system which is discussed below. It is important to understand that the circumference adjuster is provided, as mentioned before, to increase or decrease the needle 111 radial circumferential motion in order to make available changes in the needle and/or the wound to be sutured.

The circumferential motion of the interactive portions is achieved while providing rotational motion at the interactive portions 2. The first embodiment makes use of a rotational system to perform said rotational motion wanted at the interactive portion 2. The rotational system for the first embodiment comprises a main gear 5a driven by a central shaft 5b. The central shaft 5b comprises a hollow cylinder positioned about the central axis of the device. The central shaft 5b is positioned within the frame 3 and includes a portion of the locking system at a distal end. It is important to understand that the central shaft 5b is mechanically connected to the supporting plate 6c of the locking system 6 by means of a bearing 3c, wherein said central shaft 5b rotates free about its axis without transferring the rotation to the frame. In addition the central shaft 5b is equipped with a rotational actuator such as a turning knob 5c comprising a rugged outer layer on the central shaft 5b. The turning knob 5c allows the user to apply a rotational motion to the device 1 with his or her fingers. The supporting plate 6c further comprises engaging protrusions 6f extended away from the rotational system 5 and two structural bars 3b attaching said plate 6c to the frame 3.

Figure 4:
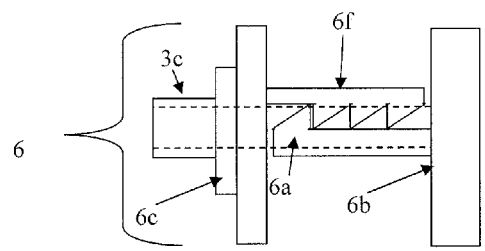
FIG. 4 shows the first embodiment's locking system components

FIG. 4 clearly discloses the locking system 6 wherein the platform 6b engage the supporting plate 6c by means of the protrusions 6a and said engaging protrusions 6f, wherein said extended pieces having hooks shapes 6a mechanically connects and fixes the circumference adjuster system 4 to the central shaft 5b.

Figure 5A:
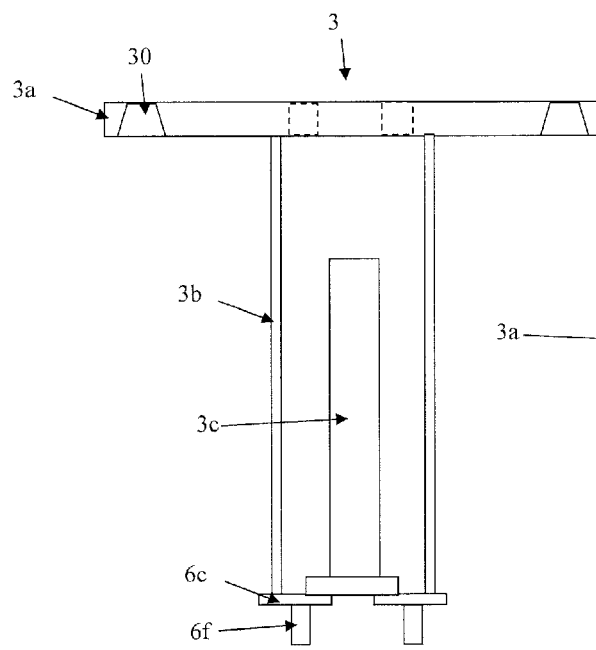
FIG. 5A-5B shows the first embodiment's frame
Figure 5B:
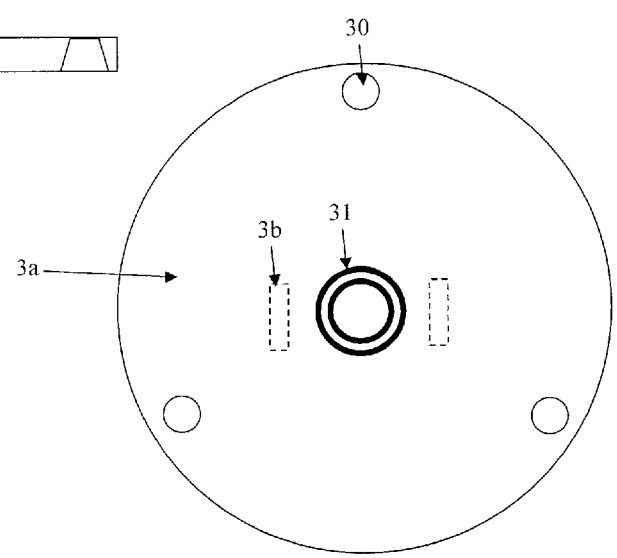

The frame, as shown in FIG. 5A-5B, comprise the central plate 3a, a supporting plate 6c, and two structural bars 3b attaching said plates. The central plate 3a, as shown in FIG. 5A, is shaped to be a flat cylindrical portion with a concentric hole. The plate 3a serves as a support for the interactive portions 2, wherein said central plates comprises pivoting ends 30 for the rods' 20,21 movement in the event a change in the circumference is desired. It has to be understood that the pivoting end 30 works in combination with the circumference adjuster 3 to provide the desired circumference or distance between the interactive portions 2. The supporting plate 6c is rigidly connected to the central plate 3a by means of the two structural bars 3b.

Figure 6A:
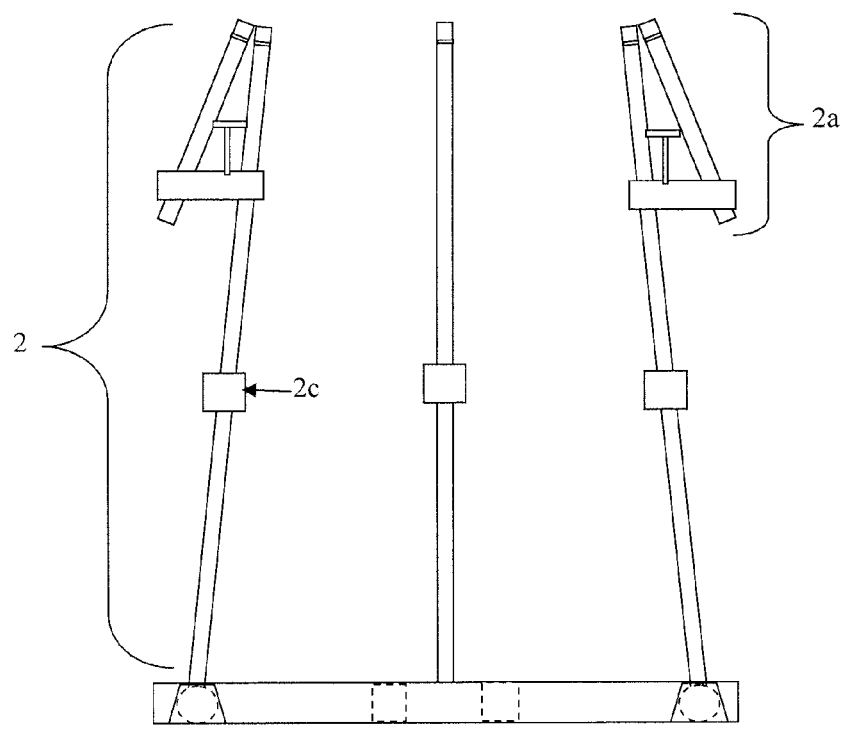
FIG. 6A-6C shows the first embodiment's interactive portion attached to a frame and first distal end components.
Figure 6B:
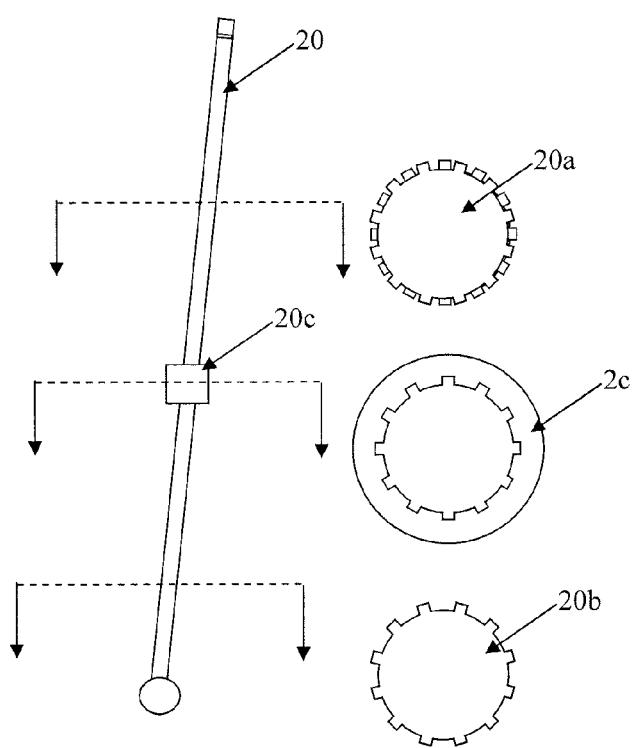
Figures 6C, 7, 8:
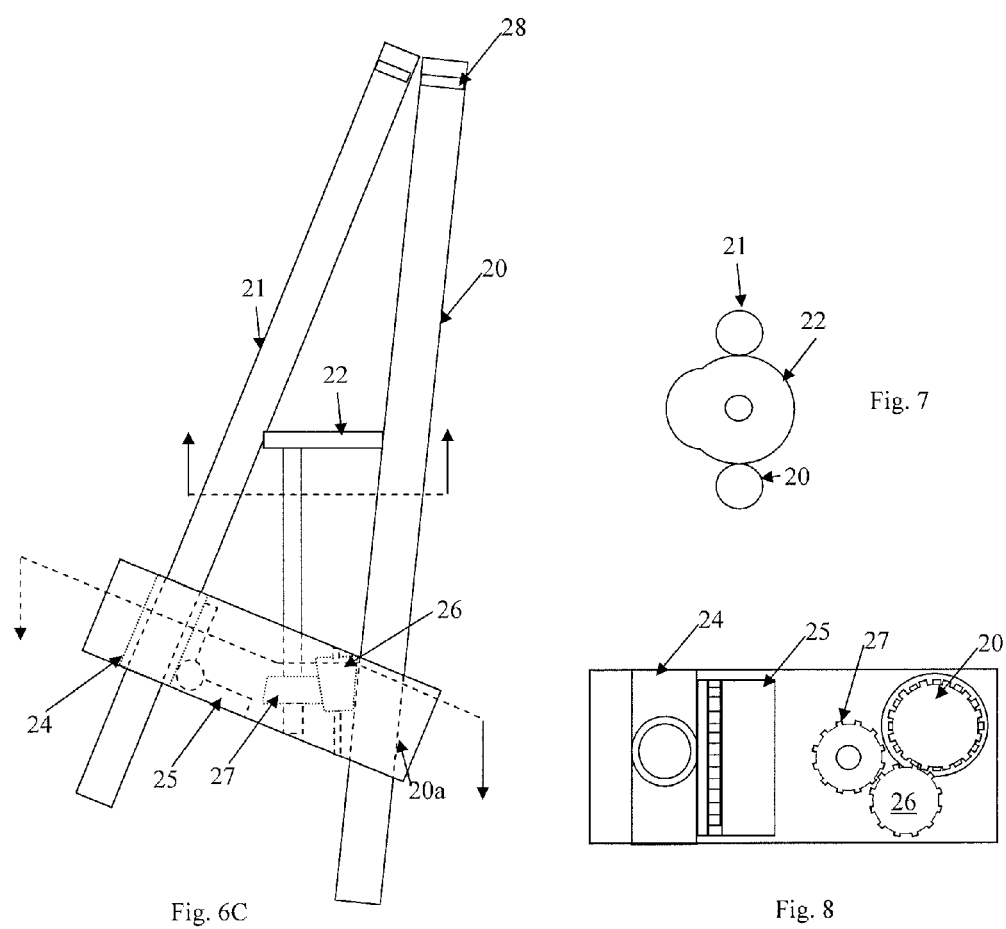
FIG. 7 shows part of the first embodiment's linear motion system
FIG. 8 shows part of the first embodiment's linear motion system with contact distal end adjustment mechanism.

FIG. 6A-6C discloses the interactive portion 2, wherein said interactive portion 2 comprises extended members, such as rods 20, 21 wherein each rod has a main body with a first distal end 2a at one extreme of said rods 20, 21 and a second distal end at the other extreme of said rods 20, 21. The first embodiment comprises a first extended member 20 and a second extended member 21, wherein the first extended member 20 works as a driven rod and the second extended member 21 works as a slave rod. The first extended member 20 transfers the rotational motion from the rotational system 5 toward the distal end 2a. The first extended end achieves the transferring of rotational motion by comprising a first distal end, a second distal end and a main body, wherein the main body in shaped to have linkages ("teeth" or "cogs") that mesh with other gear teeth, such as the main gear 5a, allowing the rotational force from said main gear 5a be transferred to the first distal end. In the instance case the main body has different ratio at the same main body, as shown in FIG. 5b, in order to vary revolutions. As mentioned before a rotation holder 2c is connected to the rod 20.

FIG. 6A-6B is more directed to the grasping needle action at the first embodiment distal end structure. The first embodiment, as mentioned, applies the grasping action at the interactive portion, more specifically at a distal end 2a of the interactive portion 2. Each contact distal end 2a comprises a driven rod 20, a slave rod 21, and a linear motion mechanism 23 to open or close each end as needed. The driven rod 20 and slave rods 21 are obliquely positioned coming into contact at their respective distal ends having fluted surface creating a needle-grasping portion or contact distal end 28, around each rod surface for better positioning of the needle 111. It is important to understand that the use of obliquely positioned rods provide a better control of the portion to be press contrary to parallel rods, wherein the area where the force is applied is bigger and therefore the contacting point of force is transmitted or distributed over the whole contacting surface.

The distance between the axis of the device and each end of the driven rods 20 is identical. That is, all the driven rods 20 lie on a common circumference. Each slave rod 21 is positioned on the same radial line as the driven rod 20, forming a separate circumference outside the first. The needle 111 is moved by the force created by the rotation of the driven and slave rods 20, 21 against each other. The needle 111 will follow a line tangent to the outer edge of the driven rod 20 and the inner edge of the slave rod 21. With the driven rods 20 forming a circumference within the circumference of the slave rods 21, the trajectory of the needle 111 follows the circumference created by the points between the driven rod 20 and slave rod 21.

The linear motion mechanism 23, as shown in FIG. 6A-6C, is located at the interactive portion distal end 2a. The linear motion mechanism, as shown in FIG. 7-8, controls the grasping force exerted over the needle 111 and the linear motion at the contact distal end 28. The linear motion mechanism 23 comprises a torsion spring 25 that maintains the contact distal end 2a in a normally closed position. On the other hand the cam 22 is designed to open the contact distal end 2a at a particular distance for a particular length of a cycle. The driven rod 20, as mentioned before, transfers the rotating motion to a first gear 26. The first gear 26 consequently transfers the rotation to a second gear 27, which is coupled to the cam 22. As the cam 22 rotates, the driven rod 20 and slave rods comes into contact with a cam 22. During the cam 22 rotations the slave rod 21 will be pushed outward by the cam 22 opening the contact distal end 2a, or pushed inward by the torsion in the spring 25 creating a linear motion of the distal end 2a.

The cam 22 is designed to open the contact distal end 2a a particular distance for a particular length of the cycle. The spring 25 comprises a torsion spring that will maintain the contact distal end 2a in a normally closed position. The driven rod 20 will rotate, transferring the rotating motion to a first gear 26. The first gear 26 will transfer the rotation to a second gear 27, which is in turn coupled to the cam 22. As the cam 22 rotates, the slave rod 21 will be pushed outward by the cam 22 opening the contact distal end 2a, or pushed inward by the torsion in the spring 25.

Figure 9:
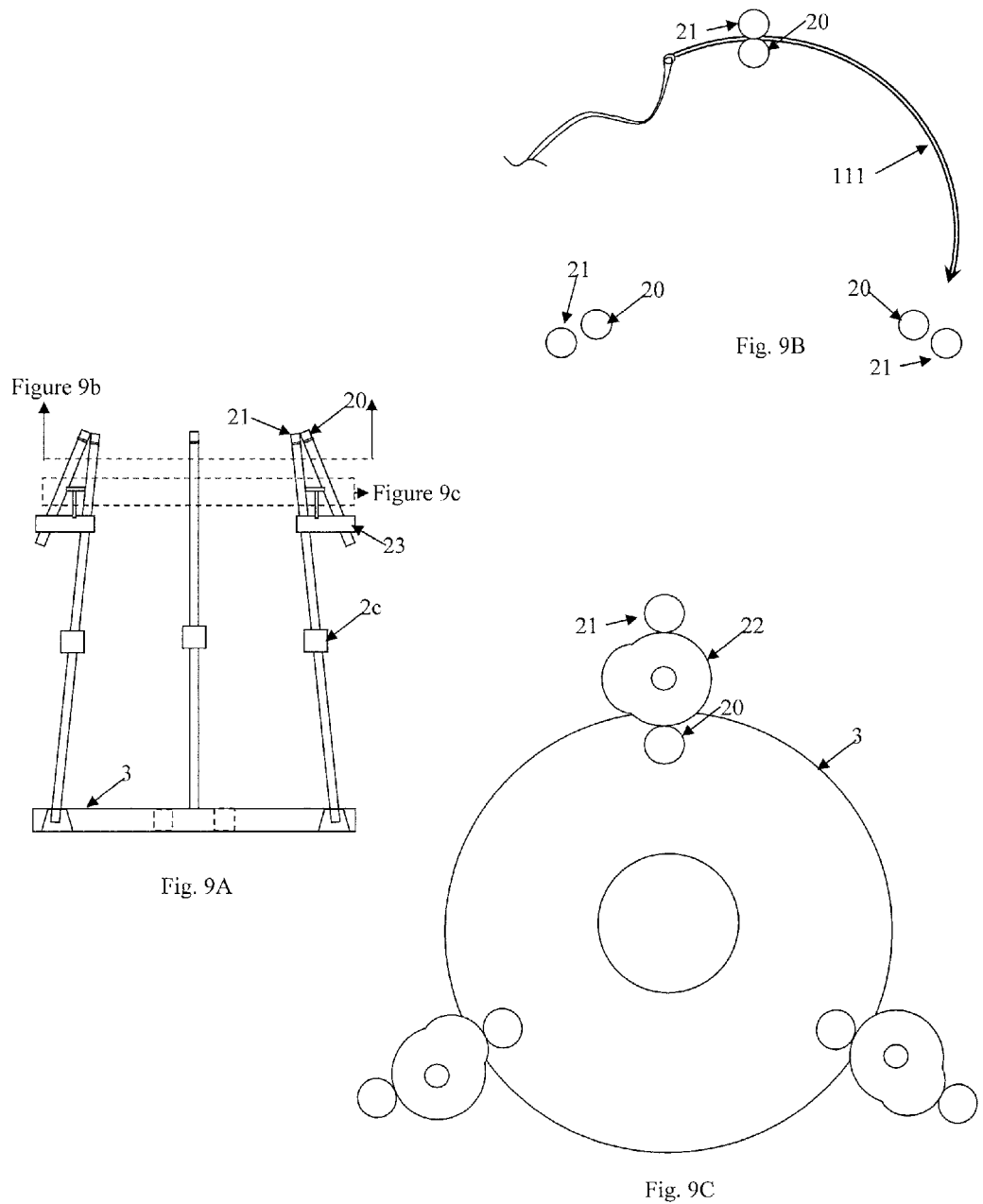
FIG. 9A-9C shows the first embodiment's sequence control mechanism.

FIG. 9A-9C shows the first embodiment comprising a sequence control system wherein said sequence control system comprises several linear motion mechanisms 23 located at all the interactive portions distal end 2a. The cam 22 of each contact distal end 2a is out of phase with one another in order to provide an opening sequence at the distal end 2a. FIG. 9C shows an example of a possible positioning scheme for a device comprising three contact distal ends 2a. The contact distal end 2a will be at the tightest position when said end is holding a needle 111, as shown in FIG. 9B. The end located in the next point in the needle's trajectory will open slightly to allow the needle 111 to comfortably enter the gap between the slave and driven rods 20, 21. As the needle 111 moves through the cycle, the contact distal ends 2a open or close as required.

It has to be understood that the length of the device may vary depending on the use. For example, a shorter device may be used by a healthcare professional suturing an open wound while longer bars could be used for devices used in laparoscopic surgeries or other uses where the wound is hard to reach. The first embodiment shows a cross-section of the central plate 3a wherein the structural bars 3b are shown having a rectangular cross-section. However, that any shape, number or variation of the structural bars here described is not beyond the scope of the invention. Further the gear ratio in the device may vary depending on the desired velocity needed, control of the needle and purpose. However, independently of gear ratio the rotation of the needle 111 around the circumference creates a suture.

Figure 10:
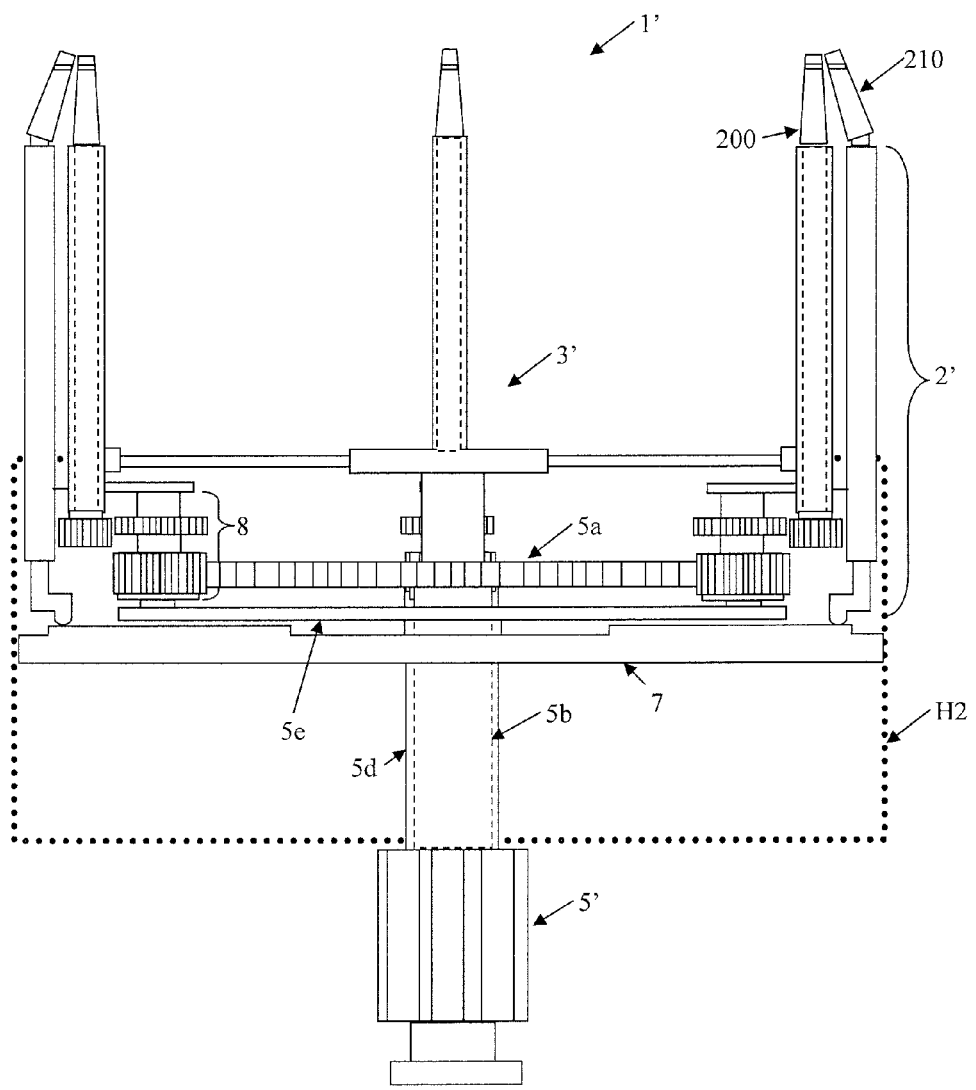
FIG. 10 shows a second embodiment employing a continuous driver device with changeable parameters.
Figure 11:
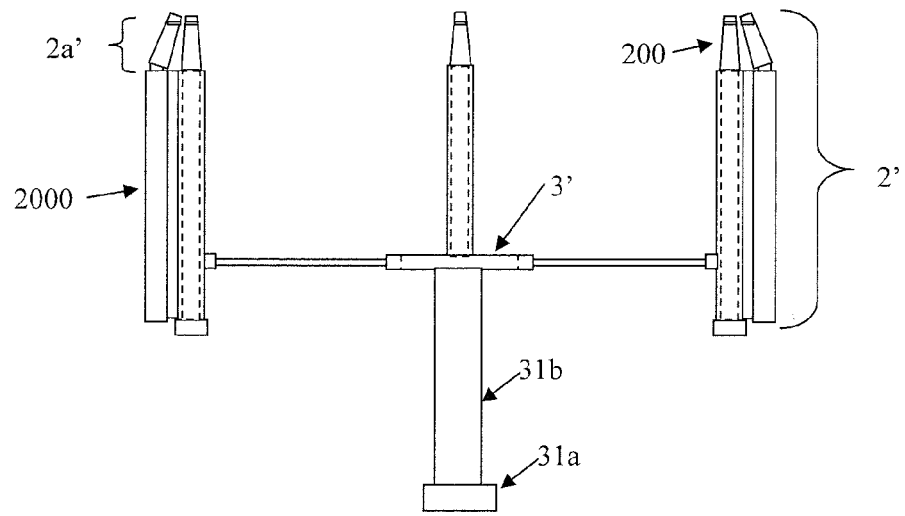
FIG. 11 shows part of the second embodiment circumference adjuster components.

FIG. 10 shows a second embodiment employing a continuous driver device 1' with changeable parameters as suturing device wherein said continuous driver device comprises a interactive portions 2', a circumference adjustment mechanism 3' which includes a locking mechanism 8, a rotational system 5', at least a linear motion system 7, a sequence control system mechanically connected rotational system 5', and a housing H2 enclosing several part of the second embodiment.

Similarly to the first embodiment 1, the device of the second embodiment 1' comprises a plurality of interactive parts 2', wherein said interactive portion comprises several extended members each with a contact distal end 2a'. Also the suture is created by rotating a needle 111 about a circumference by a number of interactive parts 2', each comprising a driven rod 200, a slave rod 210, and a contact distal end 2a'. A unified gear mechanism will provide rotation to the driven and slave rods 200, 210 and therefore to the needle 111.

The circumference adjustment mechanism 3', as shown in FIGS. 11-17 comprises a circumference change actuator 300a comprising a quasi-circular platform, several pivoting legs 300b connected to each of the interactive actuators 2', more particularly to each interactive portion housing 2000, an circumference actuator 31a, and a locking mechanism 8 presented more in detail in FIGS. 13-17.

Figure 12:
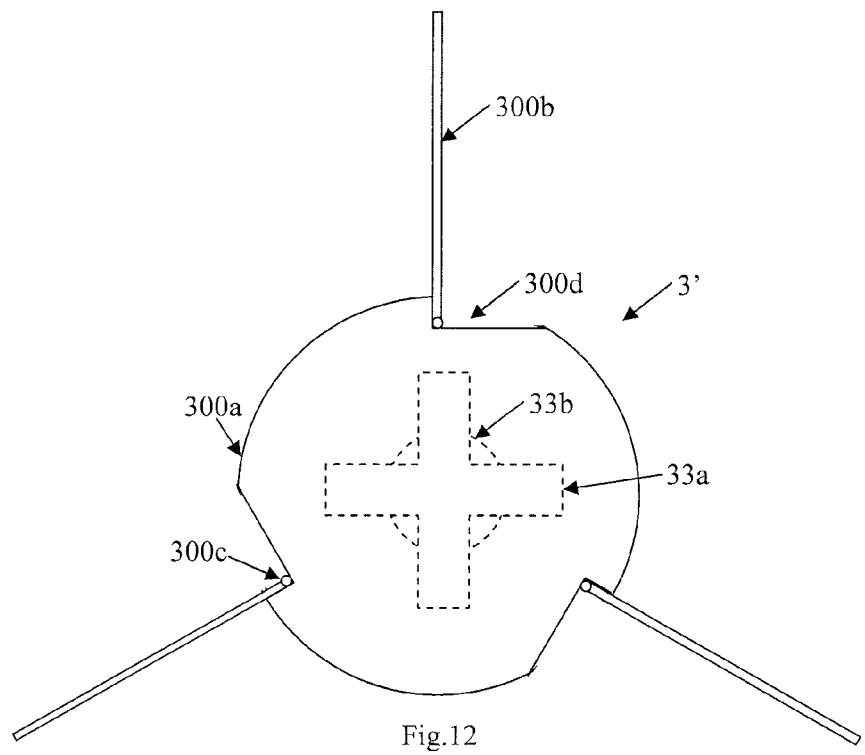
FIG. 12 shows a top view of the second embodiment circumference adjuster components.

FIG. 12 shows a top view of the circumference change actuator 300a comprising the quasi-circular platform 300a with three pivoting legs 300b, wherein said pivoting legs are attached to the platform 300a by pivoting means 300c inside a platform groove 300c. The platform groove 300c of the quasi-circular platform 300a is removed at the base of each pivoting leg 300b to allow the leg 300b to pivot from a radial position to a position parallel to the tangent of the circle. The circumference will be largest when the legs 300b are positioned in the radial position and smallest when the legs are positioned in a tangential position. The handle 31a is rigidly fastened by connection means 31b, such as a rod to the quasi-circular platform 300a.

The pivoting legs 300b of the circumference change actuator 300a are attached to the rod housing 2000. Therefore as the circumference change actuator 300a rotates counter-clockwise the circumference decreases and the rod housing 2000 is pulled inward.

Figure 13:
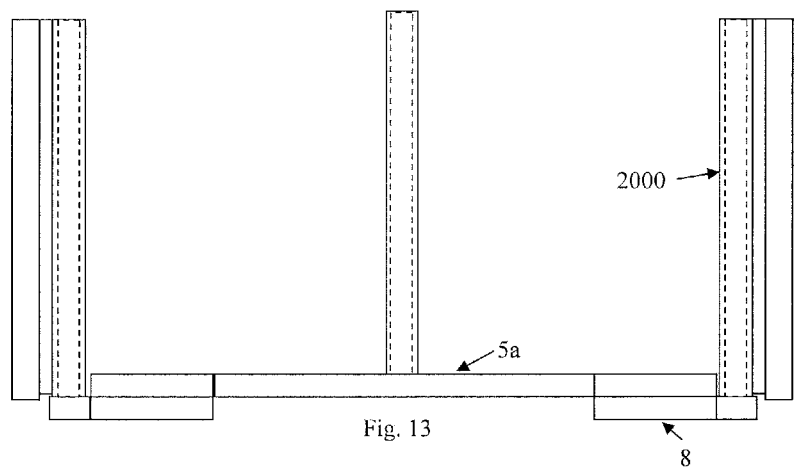
FIG. 13 shows part of the second embodiment's rotational system components
Figure 14:
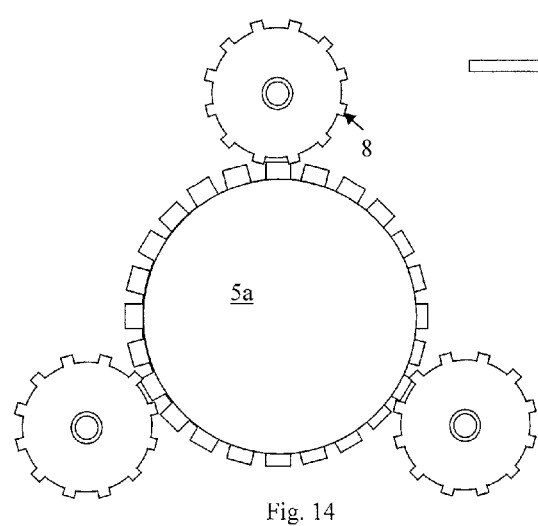
FIG. 14 shows a top view of the second embodiment's rotational system components
Figure 15:
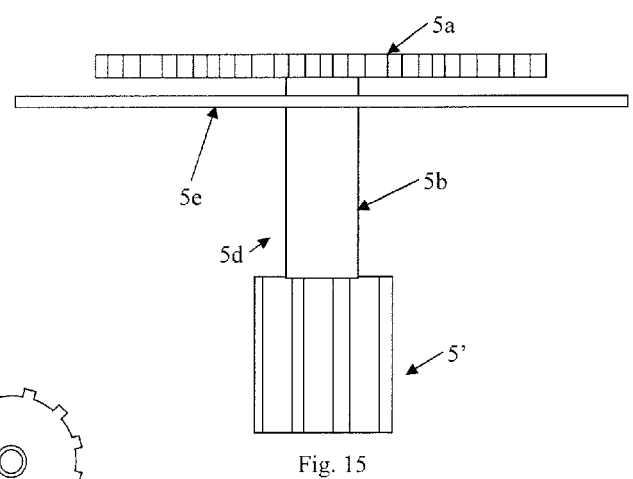
FIG. 15 shows a side view of the second embodiment's rotational system components

FIG. 13-17 shows the circumference adjustment mechanism 3' including a locking mechanism 8 in order to maintain the desired circumference for the device 1'. FIG. 13 shows a second embodiment wherein the interactive housing 2000 is mechanically coupled to single way circumference adjuster including a locking mechanism and to the rotational system by means of the main gear 5a. FIG. 14 shows the rotational system 5' coupled to the circumference adjuster 8 including a locking mechanism by means of the main gear 5a. FIG. 15 is directed to show the non-rotational plate 5e which is connected to the frame or housing H2 to support part circumference adjustment mechanism gears 8. The rotational system extension 5b' passes through said non-rotational plate 5e in order to contact the main gear 5a.

Figure 16:
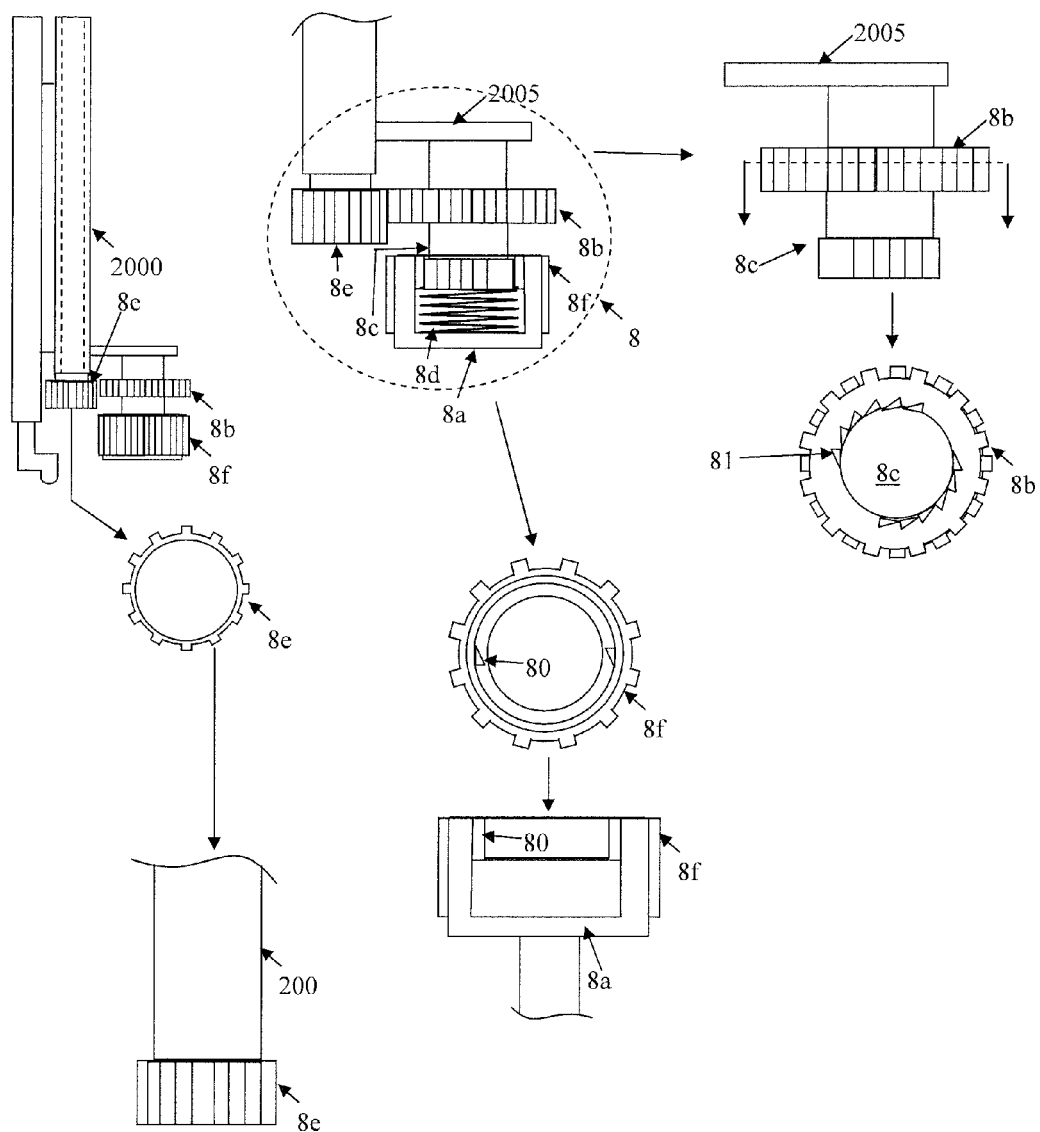
FIG. 16 shows part of the second embodiment single way circumference adjuster components in combination with elements of the second embodiment's rotational system components.

FIG. 16 shows the circumference adjustment mechanism gears 8 comprising a secondary gear 8a, a third gear 8b coupled to a rotation distal end gear 8e, a movable body 8c and a movable attachment 2005. The second gear 8a comprises a hollow body, wherein said hollow body comprises inner hooks 80 at the inner surface of the hollow body and a resilient material 8d placed inside said hollow body. The movable body 8c comprises at least two distal ends and a movable main body. One of the distal end is attached to the movable attachment 2005 in such way that the movable attachment 2005 controls the moveable body displacement in the direction parallel to the interactive housing 2000 but said moveable body 8c rotates freely on it one axis. The third gear 8b is attached to the movable main body in such way that the movable main body controls the rotation of said third gear 8b. The other movable body 8c distal end comprises hooks 81 that are combined with hollow body inner hooks 80 to lock the interactive portions 2' at a desired circumference.

During the process to adjust the second embodiment circumference the circumference actuator 31a is rotated counterclockwise. The turning action of the circumference actuator 31a is transferred to the circumference change actuator 300a resulting in the inward pulling action on the interactive housing 2000. Due to the arrangement between the hooks 81 and hollow body inner hooks 80 the no force is exerted on the second gear 8*a* resulting in a mere displacement of the housing and a difference in housing 2000 radius with respect to the center of the device 1'. It has to be understood that the resilient material, which may be attached to the moveable body 8*c*, keeps the hooks 81 and hollow body inner hooks 80 aligned. However if the movable attachment 2005 is pushed toward the second gear 8*a*, for example as the result of a force applied at the circumference change actuator 300*a*, no contact is exerted between the second gear and the moveable body. Without contacting each other there is no restraining force between the second gear 8*a* and the moveable body 8*c* and consequently the resilient material pulls the interactive housing 2000 to its starting point.

FIGS. 17 A-17C discloses the circumference adjustment mechanism gears 8 comprising a circumferential controlled system for increasing or decreasing the interactive housing radius with respect to the device center 1'. The increment or decrement in the interactive housing radius is due to the vertical displacement of the movable attachment 2005 (pushing or pulling toward the second gear 8' as the result of a force applied at the circumference change actuator 300*a*. The vertical movement or vertical displacement of the moveable attachment 2005 engages one distal end inner hooks 80 of the moveable body 8*c*' with a surface comprising hooks 81 instead of releasing the moveable body from a restraining force. Therefore the elastic force provided by the resilient material 8*d*' is limited in both directions. The second embodiment shows circumference adjustment mechanism gears 8, wherein a pulling action at the circumference change actuator permits one direction movement of the interactive portion housing 2000 and the pushing action permits one direction movement opposed to the pulling action movement of the interactive portion housing 2000. In other words FIGS. 17A-17C discloses a two way displacement gear 8. In normal condition, wherein normal conditions is defined as no pulling or pushing force applied at the moveable attachment 2005 the interactive housing can only rotates in one direction. FIG. 17C shows a moveable body with a groove to attach the moveable attachment 2005, wherein said moveable attachment permits the moveable body to rotate freely but controls the vertical displacement, as mentioned in FIG. 16. Further a cylindrical hollow second body 8*a*' is fixed to the housing H2 frame without affecting the circumference movement of the interactive portion housing 2000.

FIGS. 18A-C show in more details the interactive housing 2000, wherein said housing comprises two extended hollow cylinders having open ends, wherein a first extended cylinder 2002 serves as housing for the slave rod 210 and a second extended cylinder 2001 serves as housing for a driven rod 200. The first extended cylinder 2002 and the second extended cylinder 2001 are connected by a connecting housing body 2003, wherein said connecting housing body 2003 maintains a constant distance between the two extended hollow cylinders. The first extended hollow cylinder 2002 comprises several protrusions 2004 and a first resilient material S1, wherein said protrusions 2004 are combined with a first resilient material S1 to assist positioning substantially firmly the slave rod inside said first extended hollow cylinder 2002. Further the slave rod 210 comprises a proximal end 211 that assists with the linear displacement of said slave rod 210 which results in the grasping force exerted over the needle 111.

FIG. 19A-19F shows the second embodiment linear motion system or mechanism, wherein said system provides a platform 7, wherein the proximal ends 211 of the slave rods 210 comes into contact in order to provide a controls for the grasping force exerted over the needle 111 at the contact distal end. The platform 7 comprises an uneven surface facing the slave rods proximal ends 211. As mentioned before, the spring S1 assists to position the slave rod 210 in a particular position, more particularly the position of the slave at the contact distal end 2*a*'. During the assembling of the slave rod 210 and the spring S1 the user select if the normal position of the contact distal ends 2*a*' will be open or close. Depending on the selection user combines the assembling with the uneven platform 7 for the linear motion which results in the grasping force exerted over the needle 111.

Figure 19A:
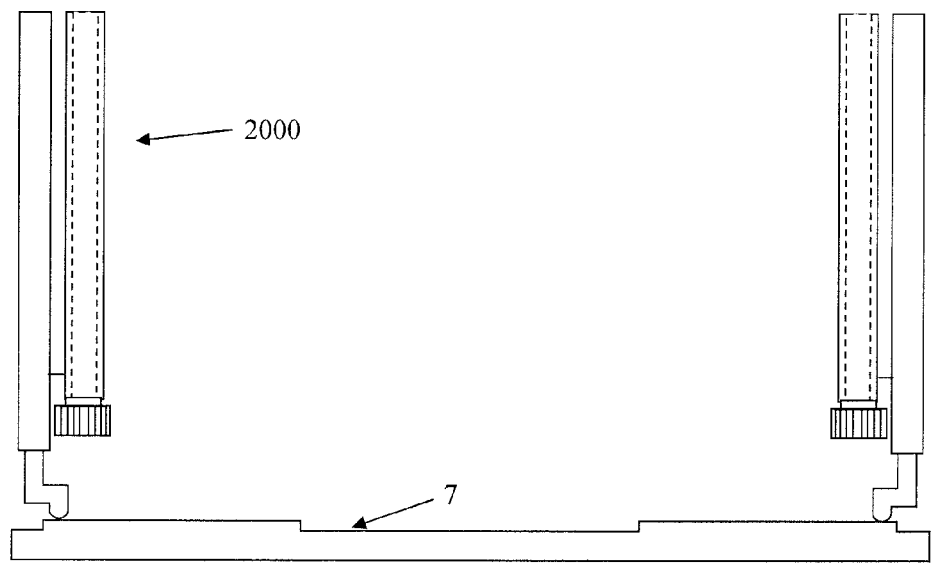
FIG. 19A-19F shows the second embodiment's linear motion system.
Figure 19B:
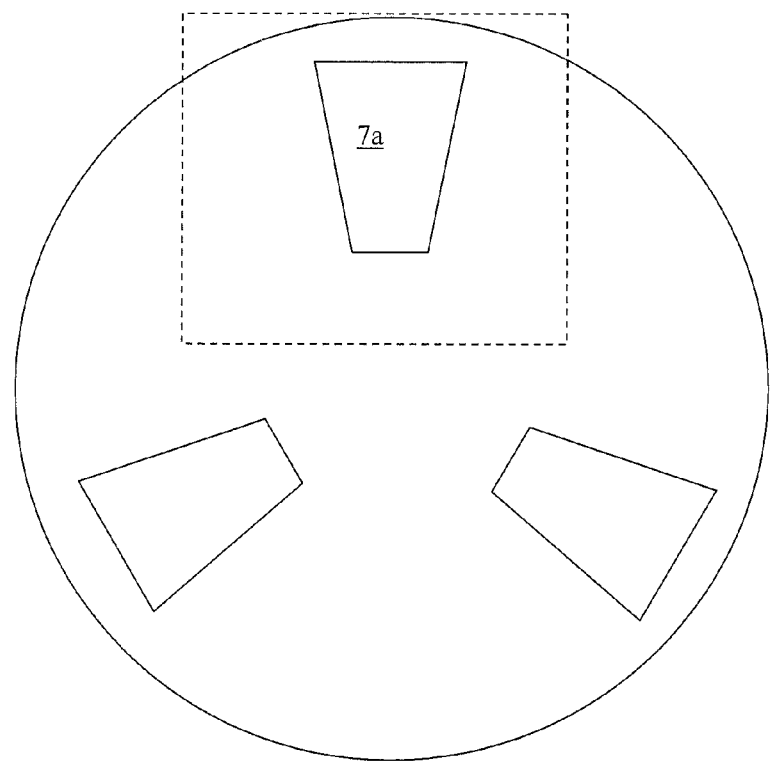
Figure 19C:
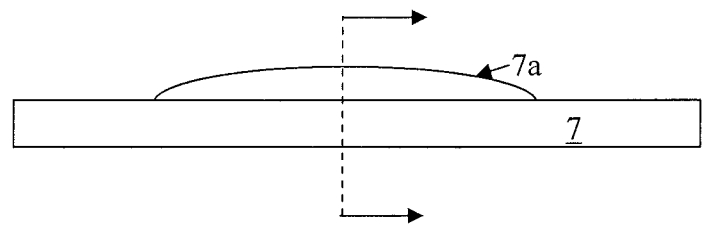
Figure 19D:
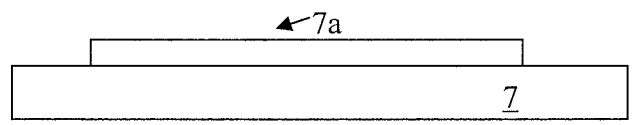
Figure 19E:
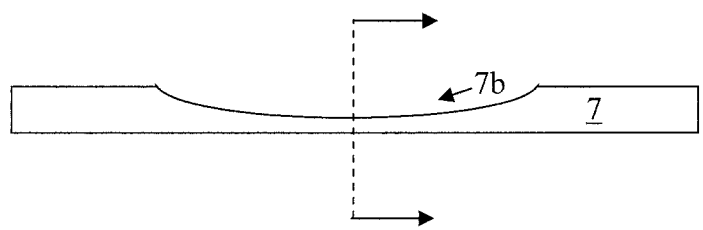
Figure 19F:
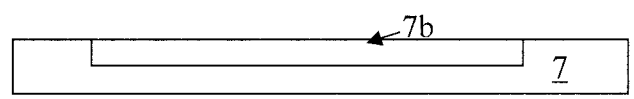

The uneven platform 7 comprises a plurality of bumps 7*a* or grooves 7*b* along its surface in order to interact with the slave rod potion in the first extended hollow cylinder 2002. For example, when the proximal end 211 of the slave rod 210 comes into contact with the bump 7*a* the slave rod 210 said slave rod 210 is pushed forward tightening the contact distal end 2*e*. When the proximal end 211 of the slave rod 210 comes into contact with the groove 7*b* the slave rod 210 will be pulled backward releasing the contact distal end 2*a*'. The bumps 7*a* or grooves 7*b* on the uneven platform 7 can be designed to open and close the contact distal ends 2*a*' sequentially. The tightness of the contact distal ends 2*a*' and the duration of the opening or closing can all be controlled with the design of the uneven platform 7. FIGS. 19C and 19E show the front views of the bump 7*a* and groove 7*b* on the uneven platform 7, respectively. FIGS. 19D and 19F show the cross-sectional areas of the bump 7*a* and groove 7*b*, respectively. The arrangement of the linear mechanism, more particular the bumps or groves assists with the open and close action at the contact distal end 28 in different points of the suture cycle. The driven rod 200 is not affected by the platform 7 and remains in a fixed position. The slave rods 210 can slide forward or backward with respect to the longitudinal axis of the device 1'. As mentioned before, the contact distal end 2*a*' will tighten when the slave rod 210 is pushed forward.

Figures 20A, 20B, 20C:
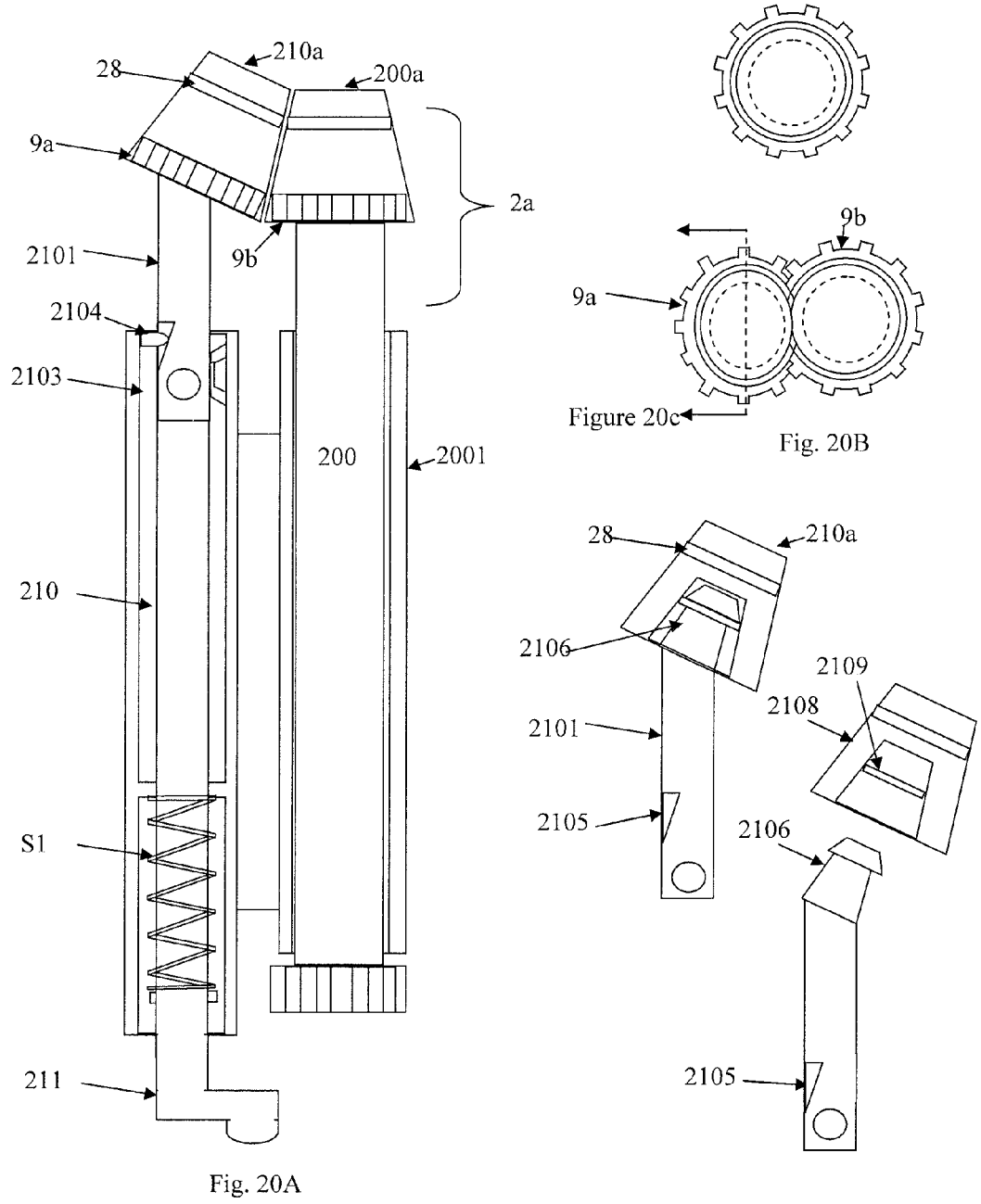
FIG. 20A-20C shows parts of the second embodiment's linear motion system with a first contact distal end adjustment mechanism.

FIGS. 20-21 are directed to the distal end arrangement of the slave rod 210 and driven rod 211. FIG. 20 shows the driven and slave rods 200, 210 are positioned in parallel to the longitudinal axis of the device 1'. The slave rod 210 is pivoted near at the contact distal end 2*a*', such that the ends of slave rods 210 are positioned obliquely with respect to the driven rods 200. FIG. 20A shows the first extended hollow cylinder 2002 comprising a protrusion 2104 extended perpendicular to the slave rod 210 and positioned at the inner surface of said hollow cylinder 2002. The main purpose of the protrusion is to be combined with the linear movement of the slave rod 210 and increase the grasping force at the contact distal end 28. A distal end resilient material 2103 is located at the inner surface of said hollow cylinder 2002 substantially facing or at least providing some resistance to the force exerted by the protrusion 2104 over the slave rod 210 when the slave rod is pushed to tightly contact the driven rod at the contact distal end 28. The third embodiment shows an arrangement that increases the force at the contact distal end when slave rod 210 is pushed toward said contact distal end 28. The slave rods 200, 210 are encased in a rigid housing 2000, and will remain parallel to the axis at all times. This feature will improve the handling of the needle 111.

Further the distal ends 210*a*, 200*a* comprises a gear mechanism 9*a*,9*b* that regulates the rotational movement between the slave distal end 210*a* and the driven distal end 200*a* as shown in FIG. 20B. FIG. 20C shows the assembling of the slave distal end 210*a*, wherein said distal end 210*a* rotates freely on distal end holder 2106. The inner wall of the slave distal end 210*a* is provided with distal end protrusion 2109 which restrains the non-rotational displacement of the slave distal end 210a. The slave distal end 210a and the driven distal end 200a are detachable and disposable. Using a device with detachable and/or disposable distal ends or interactive portions offers several benefits to the user and the device. For example, if the users need to change the distal end due to changes in needle size a simple change of distal end and/or interactive portion would be enough to continue performing the suturing process without the need of an extra device.

Figures 21A, 21B:
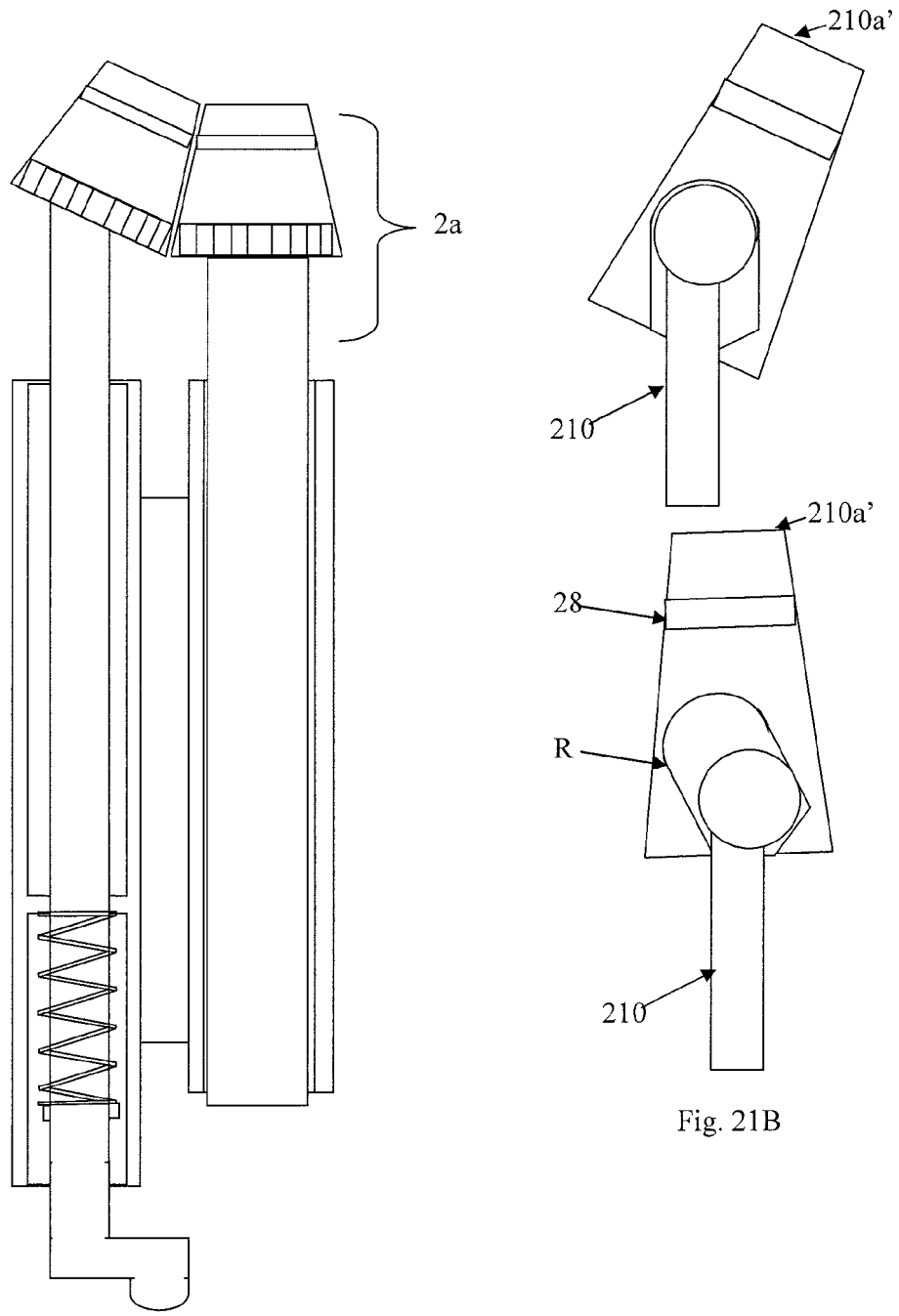
FIG. 21A-21B shows parts of the second embodiment's linear motion system with a second contact distal end adjustment mechanism.

Similarly to FIGS. 20A-20C, FIGS. 21A-21B shows a mechanism that increases the grasping force at the contact distal end 28. FIG. 21A shows a grasping mechanism wherein the grasping force at the slave contact distal end 210a' and the driven contact distal end 200a' is enhanced by the slave contact distal end 210a' inner wall R, wherein said inner wall is shaped to move away the slave contact distal end 210a' from the driven contact distal end 200a' when the linear motion at the slave rod is away from the driven contact distal end 200a', as shown in FIG. 21b.

Figure 22:
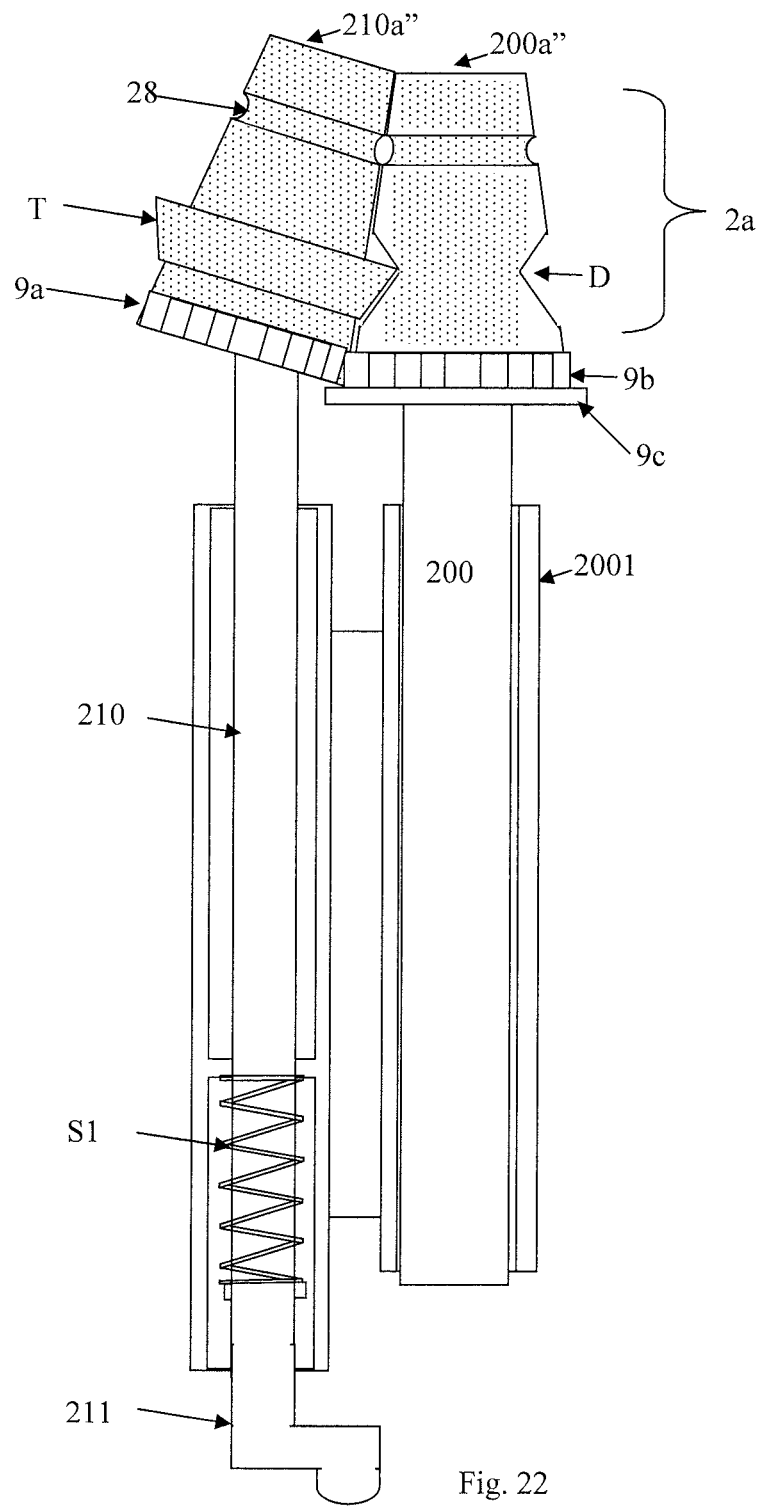
FIG. 22 shows parts of the second embodiment's linear motion system with a rearrangement of distal end for second contact distal end adjustment mechanism.

FIG. 22 shows a interactive portion distal end 2a wherein the inner wall, as shown in FIG. 21 is combined with a shaped external structure in order to assist the distal end grasping force. The slave distal end rod 210a'' comprises a distal end gear 9a at a distal end 210'' and a slave circumferential distal end extended body T, wherein said circumferential distal end extended body in combination with a driven circumferential distal end recess D assists the increases the grasping force at the contact distal end 28.

The distal ends are made of any selected material capable to perform at least the functions herein mentioned. The selection of the material depends on the field the device is going to be employed. Also the contact distal end 28 is preferred to have a surface that assist the performed action. For example, while using the device in a suturing process is preferred to have a distal end or contact distal end surface cover with a material, such as but not limited to rubber, that provide some friction over the needle in order to keep a constant displacement of said needle.

Figure 23A:
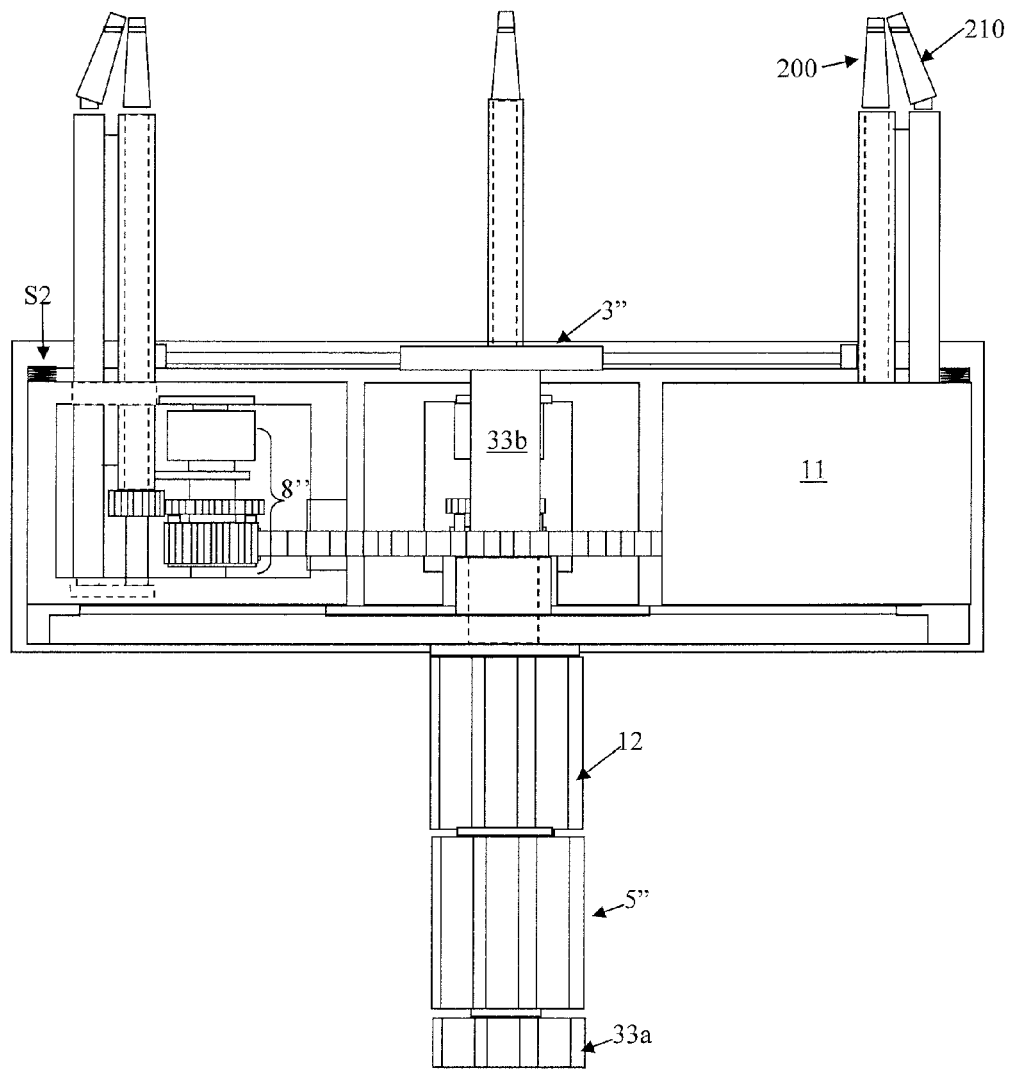
FIG. 23A-23B shows a third embodiment employing a continuous driver device with changeable parameters.
Figure 23B:
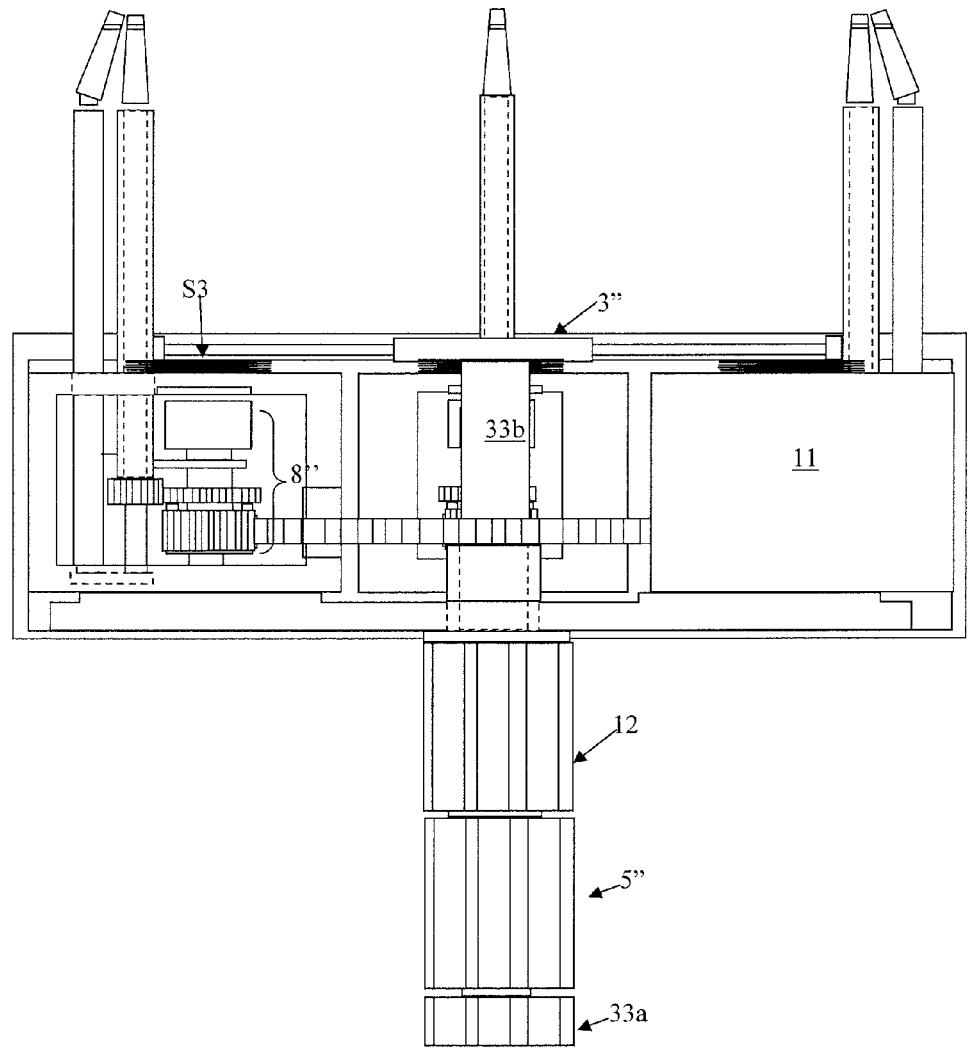

FIG. 23A and FIG. 23B discloses a third embodiment for the present invention comprising interactive portions 2'', a circumference adjuster system 3'', locking mechanism 8'', a rotational system 5'' similar to the rotational system mentioned for the second embodiment, a linear motion system, a sequence control system and housing H3. The main difference between FIGS. 23A and 23B is the position of the resilient material S2, S3 which is part of the linear motion system.

Figure 24A:
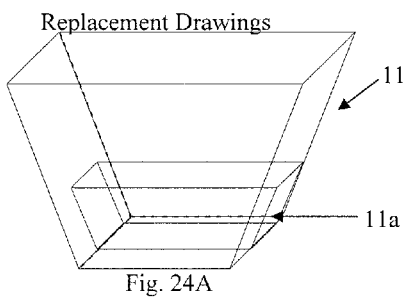
FIG. 24A-24F shows the third embodiment interchangeable box with several elements from different sub systems.
Figure 24B:
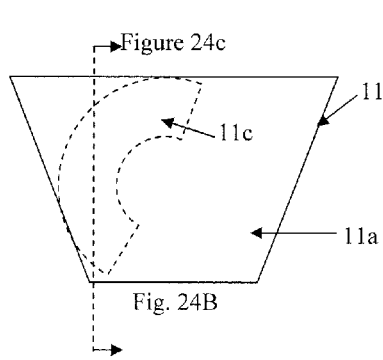
Figure 24C:
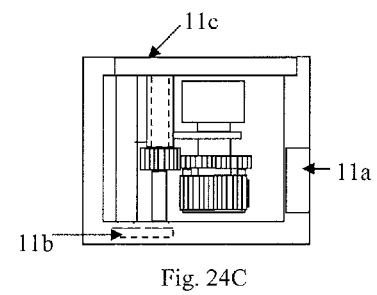
Figure 24D:
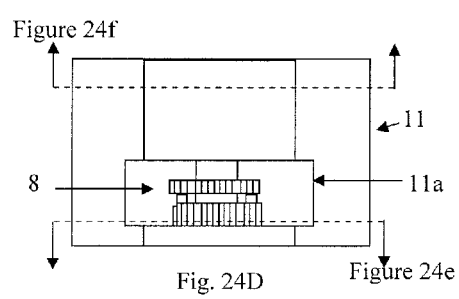
Figure 24E:
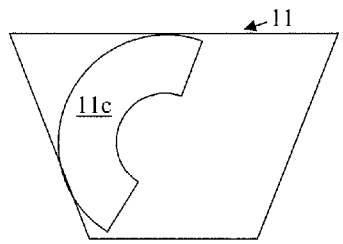
Figure 24F:
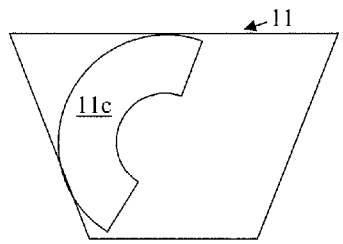

Inside said housing H3 is located an interchangeable box 11 serving as internal housing for several elements from the interactive portion 2'' and said circumference adjuster, wherein said interchangeable box is part of the linear motion elements. FIG. 24A-FIG. 24F shows the a trapezoidal shaped interchangeable box 11, as shown in FIG. 24A and FIG. 24B, comprising a hollow body, as shown in FIG. 24C, wherein said hollow body include several openings 11a, 11c and groves 11b providing an angular shapes. FIG. 25A-FIG. 25C discloses part of the elements located inside said interchangeable box 11. FIG. 25A discloses part of the interactive portion housing 2000 and therefore part of the extended bodies 200, 210 inside the interchangeable box 11. Further the interchangeable box 11, as clearly shown in FIG. 25B-25C, includes several gears 8a-8f from the circumference adjuster and part of the locking mechanism 80, 8c. Opening 11a provided at one of the interchangeable box 11 allows the access of the main gear 5a which is coupled to a rotation movement actuator by mechanical means. The openings 11c at the top of the interchangeable box 11 permits the interactive portion 2'' to extend away from the interchangeable box 11 outer surface while provides a path for the angular movement of the interactive portion housing 2000. The grooves 11c located at the inner wall of the interchangeable box 11 serve as a path for the angular movement of the interactive portion extended members 210, 200. It is important to understand that the interchangeable box may include scissor or grasping ends instead of means for suturing. In such case the interchangeable box is removed to perform an action such as cutting or grasping.

Figures 26A, 26B:
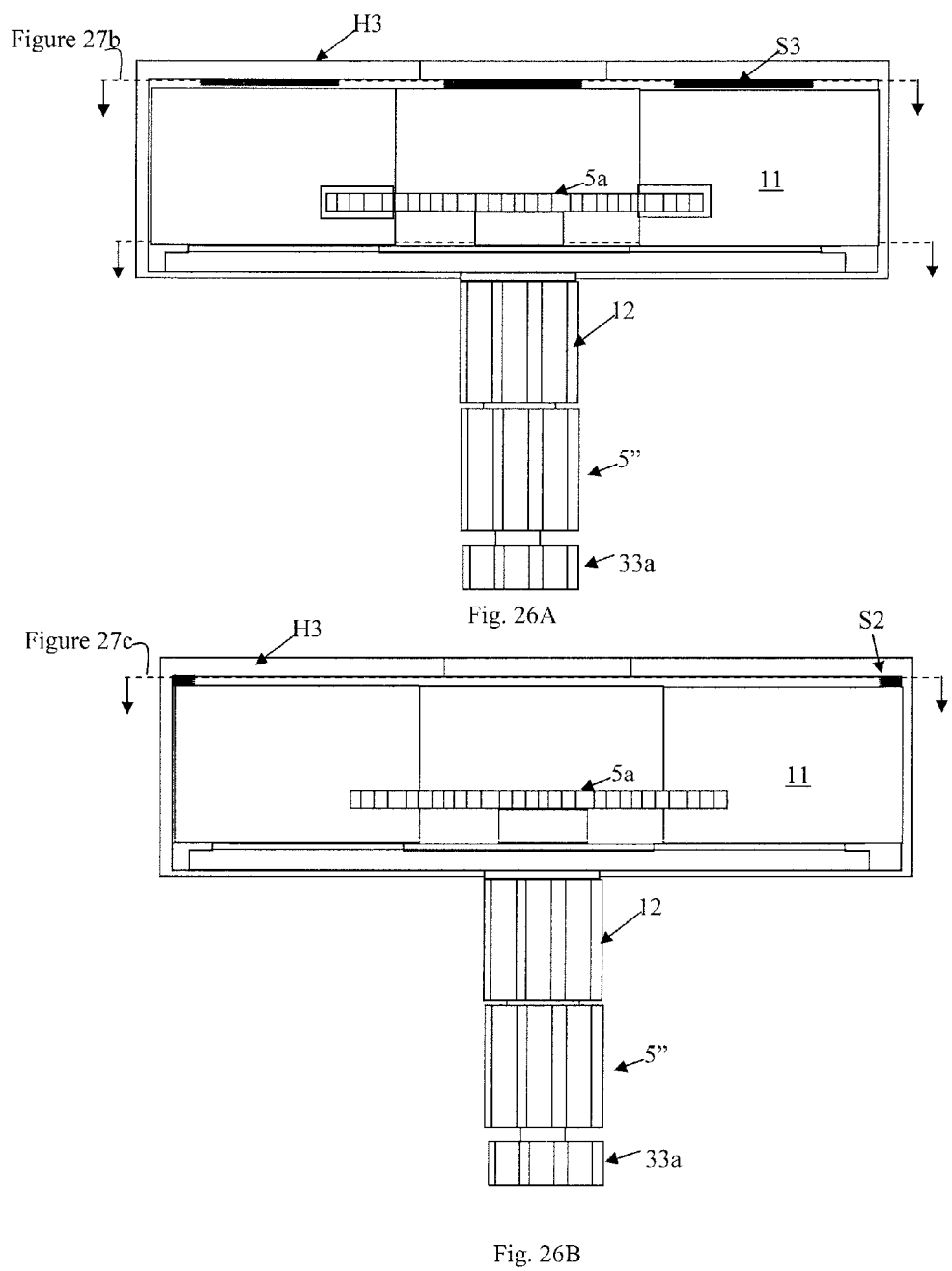
FIG. 26A-26B shows the third embodiment actuator rearrangement in combination with the interchangeable boxes.
Figure 27A:
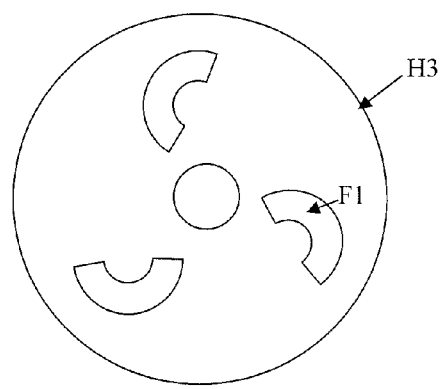
FIG. 27A-27C shows the third embodiment housing top view and several resilient material arrangements.
Figure 27C:
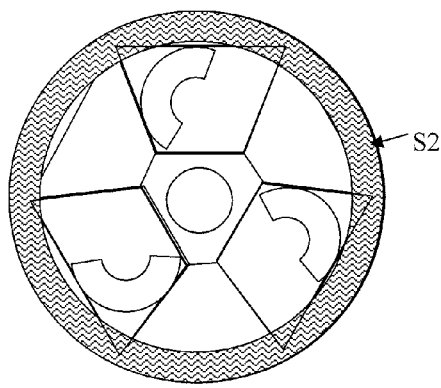
Figure 27B:
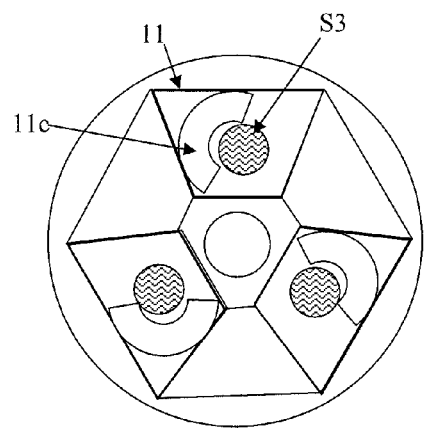

FIGS. 26A-26B and FIG. 27A-27C show, is more directed to the combination of the housing, grooves and the linear motion system. It has to be understood the interactive portion are not show for illustration purposes. The housing H3, which works together with the linear motion system encloses the interchangeable box 11 which is compressed between a resilient material S2, S3 and a pressure adjusting system as shown in FIGS. 26A-26B. FIG. 27B-FIG. 27C shows in more details how the resilient material S2, S3 is positioned inside the housing H3 with respect to the interchangeable box 11. It is important to understand that the resilient material has to contact the interchangeable box 11 in order to provide a better control of the linear motion of the interactive portion extended members 210, 200.

The pressure adjusting system comprises a pressure actuator 12 coupled to a pressure adjusting plate 7'' having a cylindrical shape, wherein said pressure adjusting plate has a protrusion 70 having a designated shape as shown in FIG. 28A-FIG. 28B. In the present case the protrusion has a C shape extending on the adjusting plate surface for approximately 240 degrees. The shape of the protrusion 70 is related to the control of sequence at the linear motion of the interactive portion. Therefore the protrusion shapes vary depending on the number of interactive portion and/or desired sequence motion.

The pressure adjusting system has a center hole that allows the connection of the rotational actuator 5'' with the main gear 5a by means of a hollow cylindrical body 50 which provides rotational motion to the interactive portions. As shown in FIG. 29A the hollow cylindrical body 50 comprises a threaded portion 51. The pressure actuator 12 is mechanically attached to said threaded portion 51 wherein said threaded portion 51 assists the vertical displacement toward the main gear 5a'' of the pressure adjusting plate for compressing the interchangeable box 11 as shown in FIG. 29B assembling of said hollow cylindrical body 50 with said pressure actuator 12. It has to be understood that the compressing action applied over the interchangeable box 11 has a direct effect over the interactive portions providing a more rigid compressing action at the interactive portions distal end 2a.

At the same side of the housing H3, as shown in FIG. 26A and FIG. 26B, and in line with the pressure actuator and rotational actuator 5'' is located the circumference actuator 33a. FIG. 30 discloses the circumference actuator 33a mechanically coupled to the circumference adjuster center portion 3'' by an extended rod 33b that transmits the turning motion of the actuator to an angular displacement of the interactive portion. As explained before the turning motion of the circumference actuator 33a produces the displacement of the interactive portions by pulling said interactive portion housing toward the circumference adjuster center portion 3'' center by means of an angular manner and therefore changing the circumference at the extended members 210, 200. The circumference adjuster center portion 3'' is connected to a rigid portion such as the housing H3 to avoid unwanted movement, for example non-rotational movement of the circumference adjuster center portion 3''.

Figure 31:
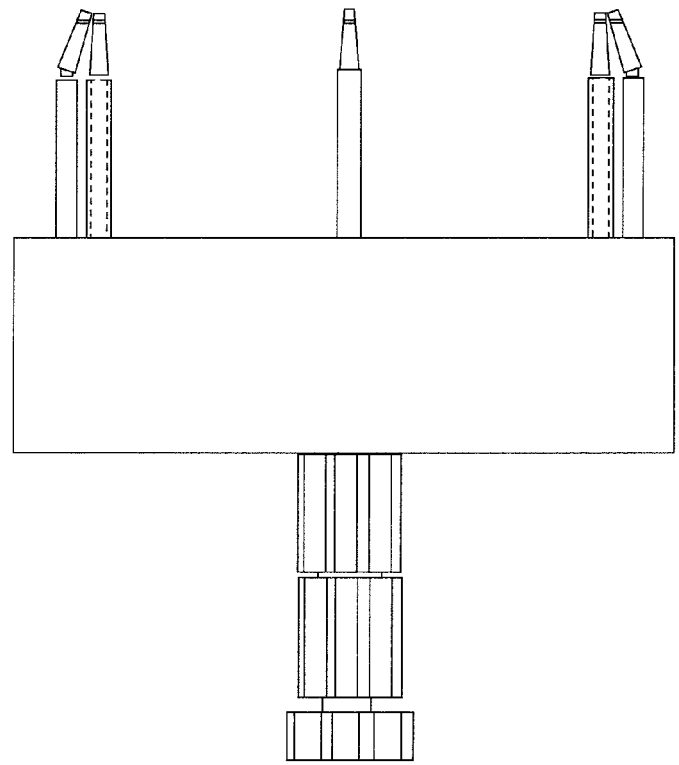
FIG. 31 shows a continuous driver device with changeable parameters in housing.
Figure 32:
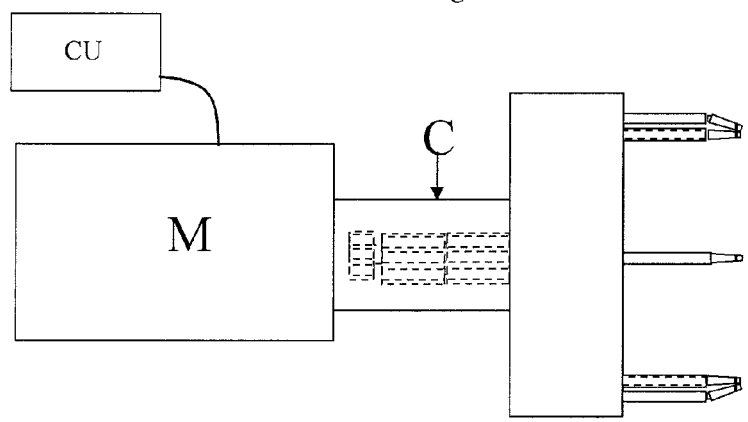
FIG. 32 shows a continuous driver device with changeable parameters coupled to a non-human motion control system with a control unit.

FIG. 31 and FIG. 32 is directed to the apparatus couple to a automatic system wherein a motor M is mechanically couple to the apparatus to provide the desired turning motion on any of the actuators in order to change any of the changeable parameter of the apparatus 1,1',1" such as circumferential distance between interactive portions, linear motion, compressing force and rotational motion at the first distal end and said interactive portions. Further the apparatus can be applied to another instrument, such as laparoscopy instruments.

Figure 33A:
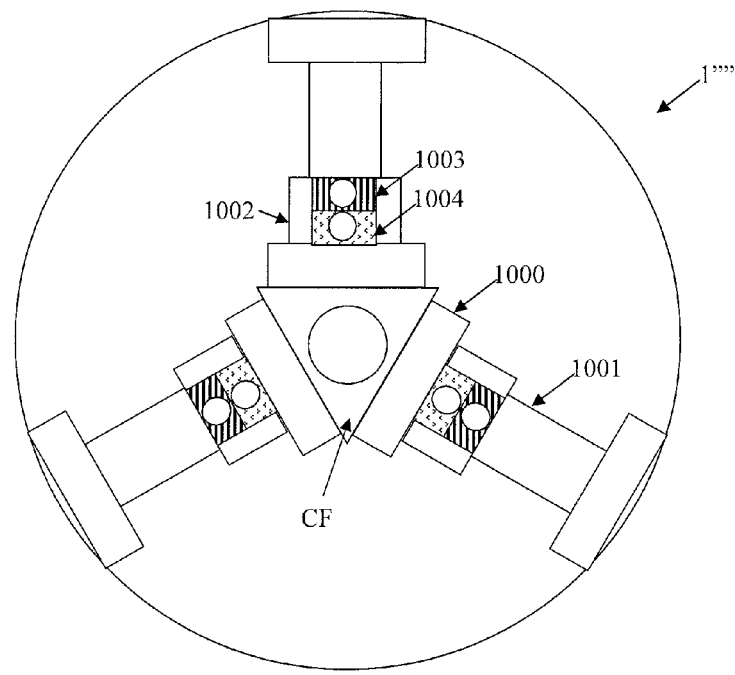
FIG. 33A-33B shows a fourth embodiment employing a continuous driver device with changeable parameters comprising electric motors.
Figure 33B:
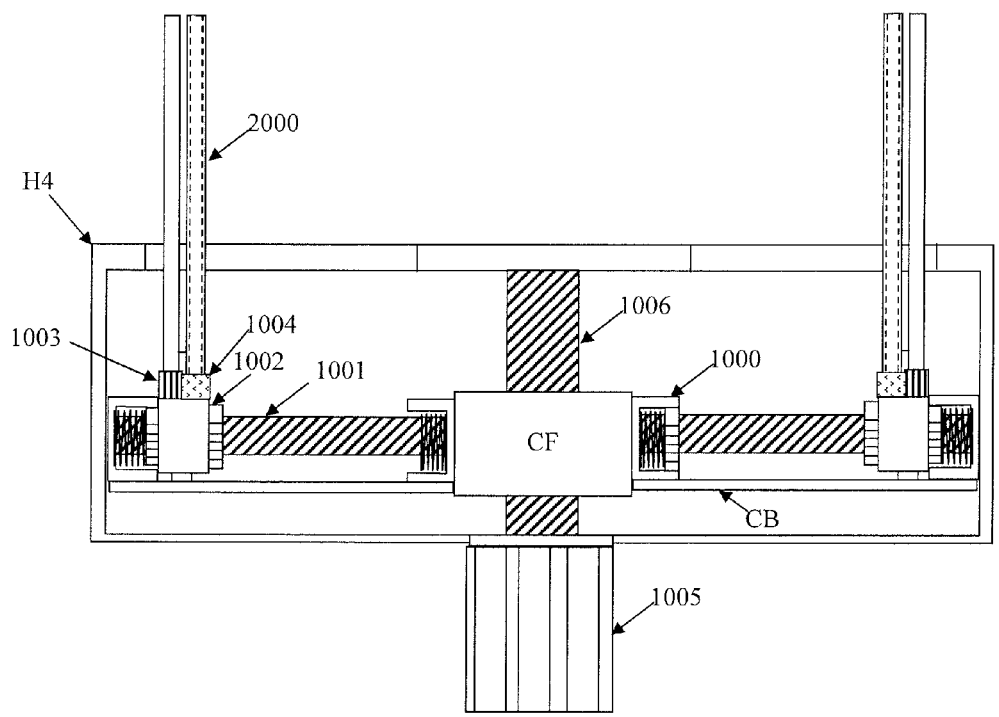

FIG. 33A and FIG. 33B shows a forth embodiment 1"" for the present invention comprising interactive portions housing 2000, a circumference adjuster system 1001, a rotational system 1004, a linear motion system 1003 and a housing H4. The current embodiment employs the use of rotational and/or linear motor to perform the same functions as explained above.

The invention is not limited to the precise configuration described above. While the invention has been described as having a preferred design or use, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patentable distinguish any amended claims from any applied prior art.

What is claimed is:

1. A continuous rotational driver with changeable parameters comprising:
    a plurality of interactive portions;
    a circumference adjuster;
    a rotational system;
    a linear motion system,
    wherein each interactive portion comprise a first extended member and a second extended member, wherein the first extended member rotates upon a first extended member's axis, wherein the first extended comprises a first distal end, a first proximal end and a first main extended member body, wherein said first main extended member body is between said first distal end and said first proximal end, wherein said first distal end comprises a first contact distal end,
    wherein the second extended member rotates upon a second extended member's axis, wherein the second extended member comprises a second distal end, a second proximal end and a second main extended member body, wherein said second main extended member body is between said second distal end and said second proximal end, wherein said second distal end comprises a second contact distal end,
    wherein the circumference adjuster comprises a circumferential actuator and a circumference adjuster mechanism mechanically connected to the interactive portion, wherein said circumferential actuator initiates a displacement between interactive portions by means of the circumferential adjuster mechanism, wherein said circumferential adjuster mechanism physically interacts with said interactive portions shifting the distance between said interactive portions distance,
    wherein the rotational system comprises a rotational actuator mechanically coupled to at least an action transmitter mechanism, wherein said action transmitter mechanism is mechanically connected to the second extended member of each interactive portion providing rotating action upon said first extended member, wherein the first extended member rotating direction is opposite to the second extended member rotating direction; and
    wherein the linear motion system comprises means for mechanically exerting a compressing force between the first contact distal ends and the second contact distal end wherein said second distal end is positioned obliquely with respect to said first distal end.

2. The continuous rotational driver of claim 1 wherein the first extended member distal end and said second extended member distal end are detachable and disposable distal ends.

3. The continuous rotational driver of claim 1 wherein said circumference adjuster mechanism change the distance between said interactive portions by angular displacement of the interactive portions.

4. The continuous rotational driver of claim 3 wherein the circumference adjuster mechanism comprises a main body with pivoting legs and a locking mechanism, wherein said locking mechanism fix the interactive portion at a selected position.

5. The continuous rotational driver of claim 4 wherein said main body comprises a rod with said pivoting legs connected to said interactive portion, wherein said pivoting legs change the interactive portion by pulling or pushing said main body in a direction perpendicular to said interactive portions.

6. The continuous rotational driver of claim 4 wherein said main body comprises a platform with pivoting legs wherein said pivoting legs are connected to said interactive portion, wherein said pivoting legs push or pull said interactive portion in an angular manner by turning said platform in a counterclockwise and counter wise direction.

7. The continuous rotational driver of claim 1 wherein said circumference adjuster mechanism change the distance between said interactive portions by linear displacement of the interactive portions.

8. The continuous rotational driver of claim 1 wherein the rotational system comprises a rotational motion actuator mechanically connected to a main gear, wherein said gear is mechanically connected to several gears to transfer said rotational motion to the interaction portion.

9. The continuous rotational driver of claim 1 wherein said linear motion comprise a plate that interact with said second extended member in a manner that a platform provides a linear movement for said second extended member exerting compressing force at the contact distal end.

10. The continuous rotational driver of claim 9 wherein said plate is an adjustable plate to provide variable compressing force at the contact distal end of each interactive portion.

11. The continuous rotational driver of claim 9 wherein said plate rotates to provide a sequence of variable compressing force at the contact distal end of each interactive portion.

12. A continuous suture rotational needle driver with changeable parameters comprising:
    a plurality of interactive portions;
    a circumference adjuster;
    a rotational system;
    a linear motion system, wherein the interactive portions each comprise several extended bodies comprising a proximal end, a distal end, and a main body between said proximal and distal ends, wherein each interactive portion comprises two rods as the extended bodies that will rotate in opposite directions, wherein the circumference adjuster comprises means for changing the circumferential distance between the interactive portions by angular and/or linear displacement of the interactive portions, wherein the rotational system comprises a system to rotate at least one extended body of each interactive portion upon itself, and wherein the linear motion system comprises a means for linear motion to provide motion to at least one of the extended bodies with respect to the remaining extended bodies of the particular interactive portion.

13. The driver of claim 12, wherein the circumference adjuster comprises gears, bearings and actuators.

14. The driver of claim 12 wherein the rotational system comprises a rotational motion actuator mechanically connected to several gears with different ratios.

15. The driver of claim 12 wherein the interactive portions are placed in a circular formation.

16. The driver of claim 15 wherein the extended members of each interactive portion are positioned on a common radial line with respect to the circular formation of the interactive portions.

17. The driver of claim 12, wherein a needle will rotate between the extended bodies of the interactive portions, such that the trajectory of the needle through all the interactive portions completes one cycle of a suturing procedure.

18. The device of claim 17 wherein the suturing cycle can be completed with a single motion.

19. A continuous rotational driver with changeable parameters comprising:
a plurality of interactive portions;
a circumference adjuster;
a rotational system;
a linear motion system, wherein each interactive portion comprise a first extended member and a second extended members, wherein the first extended member comprises a first distal end, a first proximal end and a first main extended member body, wherein said first main extended member body is between said first distal end and said first proximal end, wherein said first distal end comprises a first contact distal end, wherein the second extended member comprises a second distal end, a second proximal end and a second main extended member body, wherein said second main extended member body is between said second distal end and said second proximal end, wherein said second distal end comprises a second contact distal end, wherein the circumference adjuster comprises a circumferential actuator and a circumference adjuster mechanism mechanically connected to the interactive portion, wherein said circumferential actuator initiates a displacement between interactive portions by means of the circumferential adjuster mechanism, wherein said circumferential adjuster mechanism physically interacts with said interactive portions shifting the distance between said interactive portions distance, wherein the rotational system comprises a rotational actuator mechanically coupled to at least an action transmitter mechanism, wherein said action transmitter mechanism is mechanically connected to the second extended member of each interactive portion providing rotating action upon said first extended member; and wherein the linear motion system comprises means for mechanically exerting a compressing force between the first contact distal ends and second contact distal end wherein said first distal end rotate in opposite directions of the second distal end.

20. The continuous rotational driver of claim 1 wherein the first extended member distal end interacts with second extended member first distal end, wherein said second end positioned obliquely with respect to said first extended.

* * * * *